United States Patent
Thomas et al.

(10) Patent No.: US 11,578,050 B2
(45) Date of Patent: *Feb. 14, 2023

(54) BIOFLAVONOID COATED MATERIALS

(71) Applicant: CITROX BIOSCIENCES LIMITED, Cambridge (GB)

(72) Inventors: Howard Thomas, Cambridge (GB); Denis Dowling, Dublin (IE); Marie G. Katsikogianni, Dublin (IE)

(73) Assignee: Citrox Biosciences Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/062,535

(22) Filed: Oct. 2, 2020

(65) Prior Publication Data

US 2021/0120815 A1    Apr. 29, 2021

Related U.S. Application Data

(63) Continuation of application No. 15/881,282, filed on Jan. 26, 2018, now Pat. No. 10,791,735, which is a (Continued)

(30) Foreign Application Priority Data

Aug. 24, 2012 (GB) ........................ 1215171
Oct. 19, 2012 (GB) ........................ 1218829

(51) Int. Cl.
*C07D 311/32* (2006.01)
*C08J 7/06* (2006.01)
(Continued)

(52) U.S. Cl.
CPC ............ *C07D 311/32* (2013.01); *A01N 25/10* (2013.01); *A01N 43/16* (2013.01); *A23B 4/10* (2013.01);
(Continued)

(58) Field of Classification Search
None
See application file for complete search history.

(56) References Cited

U.S. PATENT DOCUMENTS 2,883,322 A    4/1959  Whipple
3,227,614 A    1/1966  Scheuer
(Continued)

FOREIGN PATENT DOCUMENTS

AU    2007100851 A4    11/2007
DE    10234768 A1    2/2004
(Continued)

OTHER PUBLICATIONS

Cagri—Antimicrobial edible films & coatings—J.Food Protection—2004 (Year: 2004).*
(Continued)

*Primary Examiner* — John Vincent Lawler
(74) *Attorney, Agent, or Firm* — FisherBroyles LLP; Victoria L. Boyd; Adelaide Leitzel

(57) ABSTRACT

Polymeric materials are described which have a bioflavonoid coating, the bioflavonoid content of the coating comprising at least naringin and neohesperidin. The use of such coated polymeric materials is also described as well as the process for making the coated polymeric materials.

7 Claims, 12 Drawing Sheets

Figure 1:
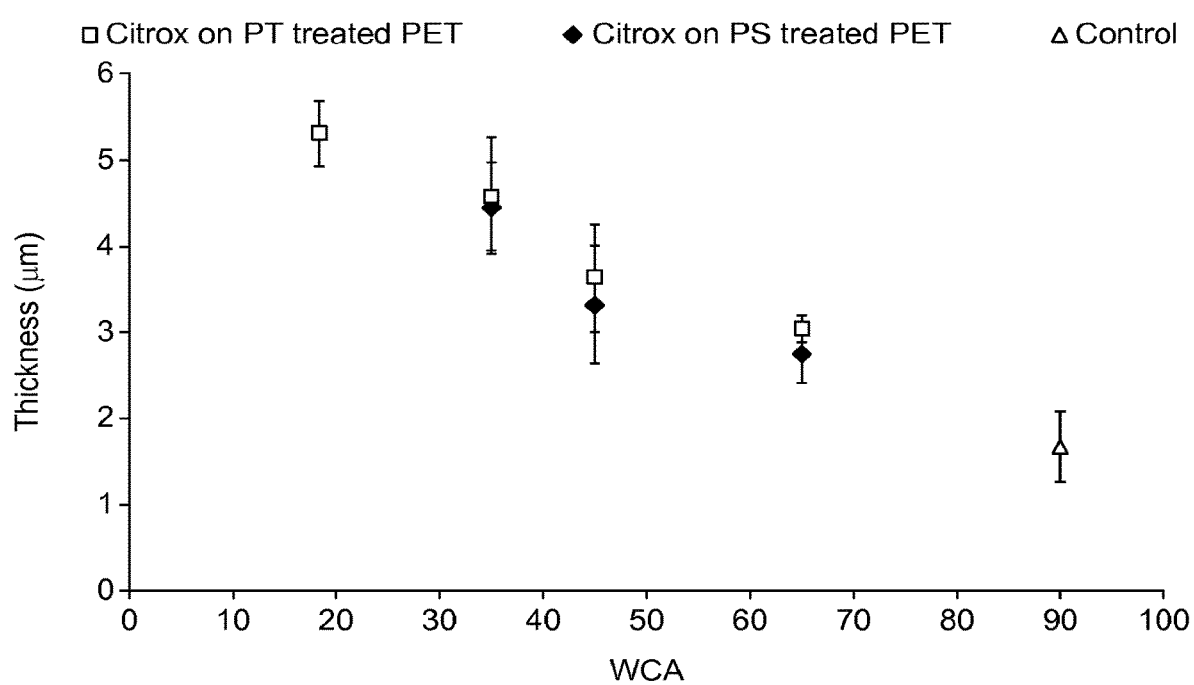
Figure 2:
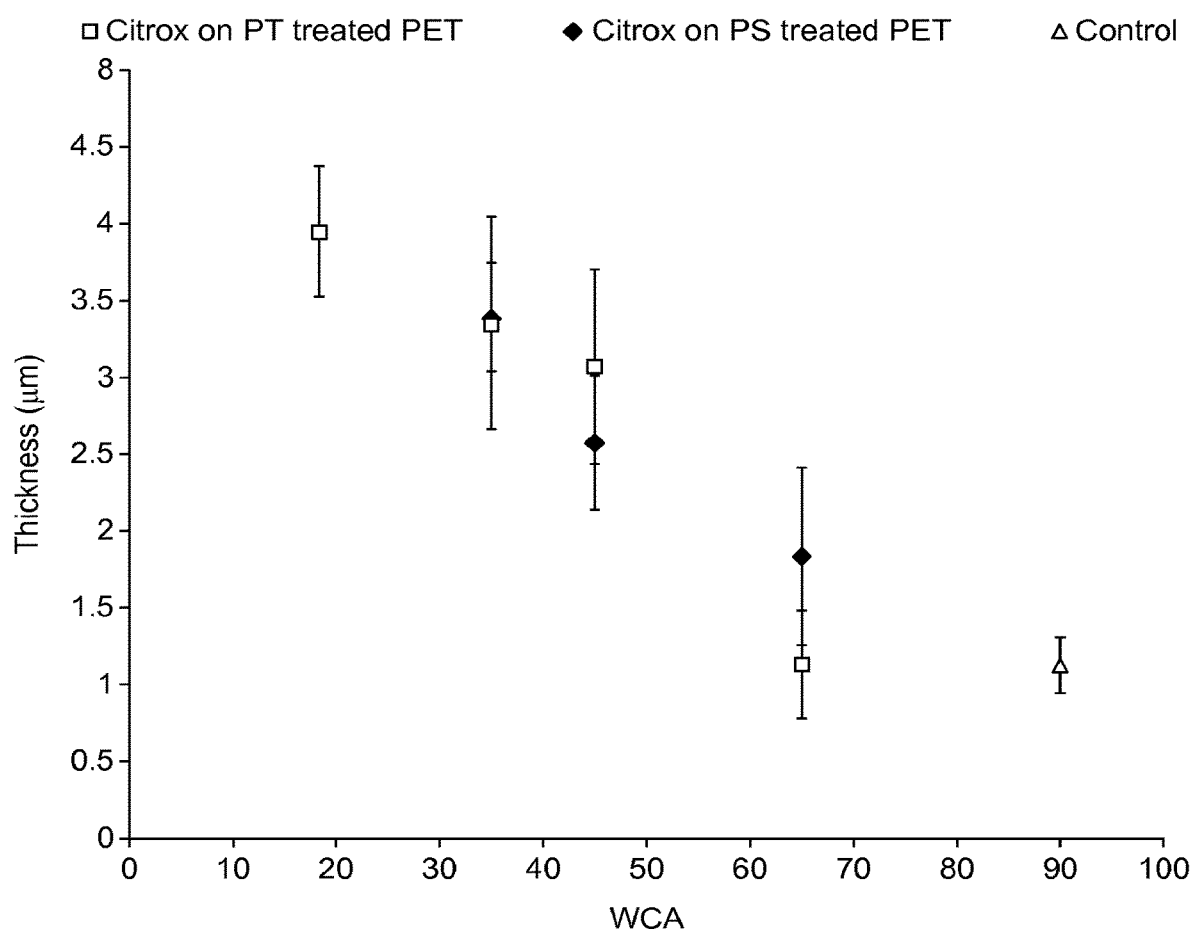

Related U.S. Application Data continuation of application No. 14/422,760, filed as application No. PCT/GB2013/052217 on Aug. 22, 2013, now Pat. No. 9,878,840.

(51) Int. Cl.

| | | |
|---|---|---|
| *D06M 15/03* | (2006.01) | |
| *D06M 13/12* | (2006.01) | |
| *D06M 16/00* | (2006.01) | |
| *D06M 13/10* | (2006.01) | |
| *D06M 10/02* | (2006.01) | |
| *A01N 25/10* | (2006.01) | |
| *A01N 43/16* | (2006.01) | |
| *A23B 4/10* | (2006.01) | |
| *B05D 1/02* | (2006.01) | |
| *B05D 1/18* | (2006.01) | |
| *B65D 65/42* | (2006.01) | |
| *B65D 81/28* | (2006.01) | |
| *C09D 5/14* | (2006.01) | |
| *A41B 11/00* | (2006.01) | |
| *A41D 13/12* | (2006.01) | |
| *D06M 13/165* | (2006.01) | |
| *C08J 7/12* | (2006.01) | |

(52) U.S. Cl.
CPC .......... *A41B 11/00* (2013.01); *A41D 13/1236* (2013.01); *B05D 1/02* (2013.01); *B05D 1/18* (2013.01); *B65D 65/42* (2013.01); *B65D 81/28* (2013.01); *C08J 7/065* (2013.01); *C09D 5/14* (2013.01); *D06M 10/025* (2013.01); *D06M 13/10* (2013.01); *D06M 13/12* (2013.01); *D06M 13/165* (2013.01); *D06M 15/03* (2013.01); *D06M 16/00* (2013.01); *C08J 7/123* (2013.01); *Y10T 428/24355* (2015.01); *Y10T 428/265* (2015.01); *Y10T 428/3179* (2015.04); *Y10T 428/3188* (2015.04); *Y10T 428/31971* (2015.04)

(56) References Cited

U.S. PATENT DOCUMENTS

| | | | |
|---|---|---|---|
| 3,283,357 A | 11/1966 | Decker | |
| 3,309,299 A | 3/1967 | Mantell | |
| 3,633,703 A * | 1/1972 | Littmann | A61B 5/02233 181/137 |
| 3,878,840 A | 4/1975 | Esbelin | |
| 4,865,855 A | 9/1989 | Hansen | |
| 4,897,304 A | 1/1990 | Hossain | |
| 5,238,749 A * | 8/1993 | Cueman | B05D 1/06 424/409 |
| 5,265,595 A * | 11/1993 | Rudolph | A61B 5/097 128/204.18 |
| 5,334,388 A | 8/1994 | Hoang | |
| 5,749,875 A | 5/1998 | Puddu | |
| 6,325,969 B1 | 12/2001 | Aamodt | |
| 6,368,361 B1 | 4/2002 | Yayabe | |
| 6,488,948 B1 | 12/2002 | Danieli | |
| 6,749,875 B2 | 6/2004 | Selleck | |
| 7,588,820 B2 * | 9/2009 | Berg | A47J 36/027 428/323 |
| 9,878,840 B2 | 1/2018 | Thomas | |
| 2002/0176882 A1 | 11/2002 | Schur | |
| 2003/0203082 A1 | 10/2003 | Daniher et al. | |
| 2004/0161450 A1 | 8/2004 | Buder | |
| 2004/0226771 A1 | 11/2004 | Werblud | |
| 2005/0123528 A1 | 6/2005 | Gorton et al. | |
| 2005/0220907 A1 * | 10/2005 | Theoharides | A61K 31/7008 424/769 |
| 2006/0127457 A1 | 6/2006 | Buchalter | |
| 2007/0237807 A1 | 10/2007 | Luu et al. | |
| 2008/0092909 A1 * | 4/2008 | Hahne | A41D 13/1192 128/863 |
| 2008/0226485 A1 | 9/2008 | Park et al. | |
| 2008/0226495 A1 | 9/2008 | Sparks | |
| 2008/0295843 A1 * | 12/2008 | Haas | A41D 13/1192 128/206.28 |
| 2009/0019563 A1 | 1/2009 | Noro et al. | |
| 2009/0321552 A1 | 12/2009 | Hada | |
| 2010/0101605 A1 | 4/2010 | Saint Victor | |
| 2010/0129302 A1 * | 5/2010 | Ahlnas | A61K 8/63 424/59 |
| 2011/0017631 A1 | 1/2011 | Sheasley | |
| 2011/0065798 A1 | 3/2011 | Hoang et al. | |
| 2011/0203944 A1 | 8/2011 | Singer | |
| 2011/0294750 A1 | 12/2011 | Thomas et al. | |
| 2012/0100231 A1 | 4/2012 | Perla et al. | |
| 2012/0141569 A1 | 6/2012 | Lee | |
| 2012/0207806 A1 | 8/2012 | Lopesio | |
| 2013/0158128 A1 | 6/2013 | Topolkaraev | |
| 2015/0230465 A1 | 8/2015 | Thomas | |
| 2015/0232252 A1 | 8/2015 | Thomas et al. | |

FOREIGN PATENT DOCUMENTS

| | | | |
|---|---|---|---|
| EP | 0350275 A2 | 1/1990 | |
| EP | 0861662 A1 | 9/1998 | |
| EP | 1360954 A2 | 11/2003 | |
| GB | 2273291 A | 6/1994 | |
| GB | 2450536 A | 12/2008 | |
| GB | 2468836 A | 9/2010 | |
| JP | H0276809 | 3/1990 | |
| JP | H02076809 A | 3/1990 | |
| JP | H02193901 A | 7/1990 | |
| JP | H06233986 | 8/1994 | |
| JP | 2002020524 A | 1/2002 | |
| JP | 2003275250 | 9/2003 | |
| JP | 2006188672 A | 7/2006 | |
| JP | 2006257612 A | 9/2006 | |
| JP | 2006523684 A | 10/2006 | |
| JP | 2007111142 | 5/2007 | |
| JP | 2008156787 A | 7/2008 | |
| JP | 2009-041169 A | 2/2009 | |
| JP | 2009518559 A | 5/2009 | |
| JP | 2009519055 A | 5/2009 | |
| JP | 2013504553 A | 2/2013 | |
| JP | 6233986 B2 | 11/2017 | |
| WO | WO 199966961 A1 | 12/1999 | |
| WO | WO 200245515 A1 | 6/2002 | |
| WO | WO 2004091569 A2 | 10/2004 | |
| WO | WO-2005107455 A2 * | 11/2005 | A61L 29/085 |
| WO | WO 2005107455 A2 | 11/2005 | |
| WO | WO 2007125100 A1 | 11/2007 | |
| WO | WO 2008009956 A1 | 1/2008 | |
| WO | WO 2008009958 A1 | 1/2008 | |
| WO | WO 2009106889 A2 | 9/2009 | |
| WO | WO 2010089600 A1 | 8/2010 | |
| WO | WO 2010139365 A1 | 12/2010 | |
| WO | WO 2011085499 A1 | 7/2011 | |
| WO | 2011099424 A1 | 8/2011 | |
| WO | WO 2012017186 A1 | 2/2012 | |
| WO | WO-2012017186 A1 * | 2/2012 | A61K 8/498 |
| WO | WO 2014030005 A1 | 2/2014 | |
| WO | WO 2014030006 A1 | 2/2014 | |

OTHER PUBLICATIONS

Li—antimicrobial effect of surgical masks coated w-nanoparticles—2005 (Year: 2005).*
Metzger—PET and palatal implant—2009 (Year: 2009).*
Contini—PET_trays_coated_with_Citrus_extract_exh-w-conf.info—2011 (Year: 2011).*
Lore—Antimicrobial Treated Filtering Facepiece Respirators Challenged with Biological Aerosols—pub Dec. 2011 (Year: 2011).*
Blanken, What are cellulose fibers? Retrieved online at: http://diyfashion.about.com/od/dyingandscreeningprinting/f/What-Are-Cellulose-Fibers.htm. 8 pages, Feb. 8, 2011; relieved from Google 2015.

(56) References Cited

OTHER PUBLICATIONS

Cagri et al., "Antimicrobial edible films and coatings," J.Food Prot. vol. 67, p. 833-848, published 2004 (Year: 2004).
Contini—PET trays coated with Citrus extract exh—2012 (Year: 2012).
Donnelly et al., An experimental study of micron-scale droplet aerosols produced via ultrasonic atomization. Physics of Fluids. Aug. 2004;16(8):2843-2851.
European Office Action for Application No. 10702905.0, dated Jun. 11, 2012. 7 pages.
GDM Technologies Pty Ltd., Citrofresh Internet Citation, Jul. 18, 2008.
GDM Technologies Pty Ltd., Material Safety Data Sheet, Citrofresh Concentrate, Jan. 15, 2008, 3 pp.
GDM Technologies Pty Ltd., Material Safety Data Sheet, Citrofresh Hospital Grade Disinfectant Concentrate, Jan. 15, 2008, 3pp.
GDM Technologies Pty Ltd., Material Safety Data Sheet, Croplife, Jan. 15, 2008, 3pp.
Great Britain Office Action for Application No. GB0901901.9, dated Jul. 23, 2010. 4 pages.
Google date for Blanken, accessed 2015.
International Search Report for Application No. PCT/GB2010/050180, dated May 17, 2010. 4 pages.
Metzger "Polyethylene terephthalate and Pillar Palatal Implant: Its historical usage and durability in medical applications," Medtronic ENT, published 2009 (Year: 2009).
Peterson et al., Flavanones in oranges, tangerines (mandarins), tangors, and tangelos: a compilation and review of the data from the analytical literature. Journal of Food Composition and Analysis. 2006;19:S66-S73.
Trafton, "New coating for hip implants could prevent premature failure," MIT News Office, published Apr. 19, 2012, (Year: 2012).
U.S. Appl. No. 13/147,949 / 2011/0294750 / U.S. Pat. No. 9,913,470, Aug. 4, 2011 / Dec. 1, 2011 / Mar. 13, 2018, Howard Thomas.
U.S. Appl. No. 14/422,760 / 2015/0232252 / U.S. Pat. No. 9,878,840, Feb. 20, 2015 / Aug. 20, 2015 / Jan. 30, 2018, Howard Thomas.
U.S. Appl. No. 14/422,759 / 2015/0230465, Feb. 20, 2015 / Aug. 20, 2015, Howard Thomas.
U.S. Appl. No. 15/881,282 / 2018/0148243 / U.S. Pat. No. 10,791,735, Jan. 26, 2018 / May 31, 2018 / Oct. 6, 2020, Howard Thomas.
U.S. Appl. No. 17/062,535, filed Oct. 2, 2020, Marie G. Katsikogianni.
GDM Technologies Pty Ltd., Citrofresh Croplife (Plant Nutrient Synergist), Jul. 19, 2008.
Material Safety Data Sheet (MSDS), "Citric Acid", May 21, 2013.
Material Safety Data Sheet (MSDS), "Neohesperiden", Aug. 23, 2017.
MSDS, "Naringin," Jul. 14, 2015.
GDM Technologies Pty Ltd., Material Safety Data Sheet (MSDS) "Citrofresh Concentrate", Jan. 15, 2008.
Situ Biosciences LLC, Microbial Product Test Laboratory 847-483-9950; Customer Report Antimicrobial Testing, Project ID 1020-BDN-01-3, Oct. 23, 2020; prepared for AMD Medicom Inc.

* cited by examiner

BIOFLAVONOID COATED MATERIALS

RELATED APPLICATIONS

This application is a continuation of U.S. patent application Ser. No. 15/881,282, filed Jan. 26, 2018, now U.S. Pat. No. 10,791,735, which is a continuation U.S. patent application Ser. No. 14/422,760, filed Feb. 20, 2015, now U.S. Pat. No. 9,878,840, which is a 35 U.S.C. § 371 filing of International Patent Application No. PCT/GB2013/052217, filed Aug. 22, 2013, which claims priority to Great Britain Patent Application Nos. 1218829.8, filed Oct. 19, 2012, and 1215171.8, filed Aug. 24, 2012. The entire contents of each of the above documents are incorporated herein by reference.

The present invention relates to polymeric materials, processes for coating polymeric materials and their uses. More particularly, the invention relates to polymeric materials with a bioflavonoid coating.

Polymers make up a vast range of materials and exhibit a variety of different properties. Polymers may be synthetic, natural or semi-synthetic. Because of their properties (for example, thermal stability, strength and thermal insulation) polymeric materials have many uses and are an integral part of industry and everyday life.

Certain synthetic polymeric products would benefit from having antimicrobial properties. These include for example food packaging and the packaging of meat and soft fruits in particular, medical devices such as catheters, face masks such as respiratory masks, as well as the range of polymeric products used in hospitals, care homes and nurseries.

GB2468836 discloses compositions comprising bioflavonoid compounds. However, GB2468836 does not disclose use of the bioflavonoid composition in coating polymeric materials. Such materials do not appear attractive to the skilled person for use in providing antibacterial synthetic polymers because the bioflavonoid compositions do not easily adhere to such polymers. However, ways of overcoming this inherent difficulty have been found.

The present invention provides polymeric materials. The polymeric materials of the invention have a bioflavonoid coating.

According to a first aspect of the invention there is provided a synthetic polymeric material having a bioflavonoid coating, the bioflavonoid content of the coating comprising at least naringin and neohesperidin.

Especially preferred is when the major part of the bioflavonoid content of the coating comprises naringin and neohesperidin. Preferably, naringin and neohesperidn together form at least 50% wt/wt, more aptly at least 70% wt/wt, for example at least 75% wt/wt, for example 75%-80% wt/wt of the bioflavonoid content of the coating (excluding other biomass).

The bioflavonoid content of the coating may further comprise one or more compounds of Formula (I):

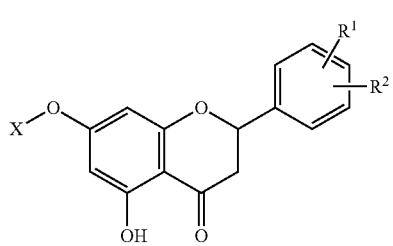

wherein $R^1$ is a hydroxyl or methoxyl and $R^2$ is hydrogen, hydroxyl or methoxyl and X is hydrogen or a saccharide.

Optionally, $R^2$ is hydrogen and $R^1$ is in the 3- or 4-position. Alternatively, $R^2$ is 3-hydroxy and $R^1$ is 4-methoxyl. Optionally, X is H. Alternatively, X is a saccharide.

Preferably X is a disaccharide. Suitable disaccharides include combinations of two monosaccharides, preferably pyranoses, linked by a glycosidic bond, for example rhamnose and glucose, for example L-rhamnose and D-glucose.

Suitable disaccharides can have the structure:

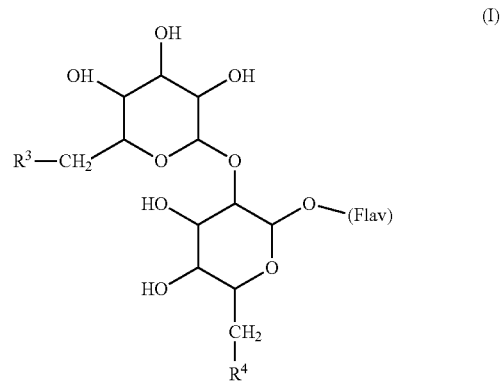

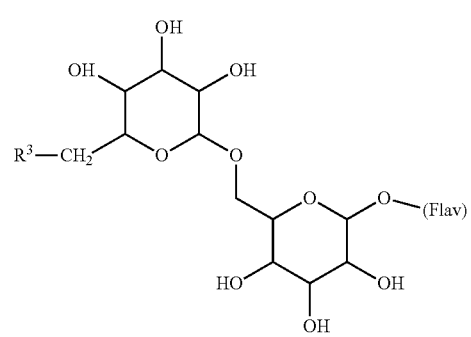

wherein one of $R^3$ and $R^4$ is H and the other OH or both are H or both are OH. Preferably $R^3$ is H and $R^4$ is OH so that the disaccharide is rutinose.

Favoured aglycones of bioflavonoids for use in this invention are the disaccharides 6-O-(alpha-L-rhamnopyranosyl)-beta-D-glucopyranose, also known as rutinose, and 2-O-(alpha-L-rhamnopyra-nosyl)-beta-D-glucopyra-rose.

Suitable compounds of Formula (I) include neoeriocitrin, isonaringin, hesperidin, neodiosmin, naringenin, poncirin and rhiofolin, in addition to naringin and neohesperidin. One of these compounds may be present in addition to naringin and neohesperidin, although a mixture of two or more of these compounds is particularly preferred.

Such mixtures can be obtained by extraction from bitter oranges and the end product is called *citrus aurantium amara* extract. Particularly preferred are the mixtures of bioflavonoid obtained from the extract of crushed whole immature bitter oranges. The mixtures can also be derived from the starting material comprised of the pith of immature, bitter (blood/red) oranges such as Seville oranges that are classed as 'inedible' and from which the pips, flesh and oily skin have been substantially removed or remain undeveloped.

Suitable mixtures can include 2, 3, 4, 5, 6, 7, 8, 9 or more compounds of Formula (I). A mixture comprising 2, 3, 4, 5, 6, 7, 8, or 9 of the above named bioflavonoids is preferable, for example containing 3, or containing 4, or containing 5, or containing 6, or containing 7, or containing 8, or containing 9 of said bioflavonoids.

It is presently believed that mixtures of such bioflavonoids have advantages over the use of a single bioflavonoid. It is particularly advantageous that extract of bitter oranges is employed without the need for isolating individual bioflavonoids. In an extract from bitter oranges biomass may be associated with up to 40-60% wt/wt, preferably about 55% wt/wt based on the weight of the bioflavonoid content of the coating. The biomass comprises pectins and other sugar derived materials. If it is desired to avoid biomass, other solubilising agents such as dextrines, for example cyclodextrin, may be employed if desired.

A particular advantage of many compositions described herein is that they may employ compounds of natural origin. Thus, for example, it is preferred to employ compounds of Formula (I) from bitter oranges. However synthetically or semi-synthetically obtained compounds may be employed if desired instead of the ones directly extracted from natural sources although this tends to be less favourable in view of cost.

The coating compositions may further comprise oleuropein. Aptly this is obtained from extraction from the leaf of the olive, for example *Olea europaea*. Such extracts typically contain 5% to 80% wt/wt, more aptly 10 to 70%, for example 20% wt/wt of oleuropein.

The wt/wt ratio of bioflavonoids to oleuropein can be 5:1 to 1:4, more aptly 2:1 to 1:2, favourably 1:2 to 1:1 and preferably 3:2. In addition to the bioflavonoid content of the coating composition, the coating composition may further comprise one or more fruit acids, for example citric acid, malic acid, and ascorbic acid. One or more of the acids are preferably neutralized with a suitable base, such as a quaternary ammonium base, for example a choline base, such as choline carbonate, bicarbonate or, preferably, hydroxide.

More preferably, citric, malic and ascorbic acids are all used in the preparation of the coating composition, and especially preferred is when these are fully neutralized to provide citrate, malate and/or ascorbate salts. Especially preferred is choline ascorbate.

It has been found that the coating composition described herein is particularly effective in the presence of one or more organic acids. In one embodiment, the coating composition further comprises one or more organic acids.

A surprisingly effective organic acid is salicylic acid or its pharmaceutically acceptable salt optionally together with a further organic acid or pharmaceutically acceptable salt.

The salicylic acid may be obtained from willow bark extract. Alternatively, methods for synthesising salicylic acid are known to those skilled in the art.

Sometimes it is preferred that the salicylic acid is in the form of the acid rather than its salt.

Similarly, a further organic acid if present is similarly in the form of the acid rather than its salt. Suitable further organic acids include acids of up to 8 carbon atoms which are monobasic (i.e. 1 $CO_2H$ group), di-basic or tri-basic acid which optionally contain 1, 2 or 3 hydroxyl groups. Such further organic acid may be one or more of citric acid, malic acid, latic acid, tartaric acid, fumaric acid and the like.

Such compositions can provide an approximately neutral or acid pH, when used, for example from 3 to 8, more aptly 3.5 to 7, for example 4 to 5.

At present it is preferred to employ salicylic acid and citric acid in the coating compositions.

Such coating compositions may include a solubilising agent, for example, salicylic acid such as a dextrin such as cyclodextrin. The compositions disclosed in WO 2012/017186 (herein incorporated by reference) are the preferred coating compositions of the present invention.

The synthetic polymer may be in the form of a film preferably with a thickness of at least 20 µm. More preferably, the film has a thickness of between 50 and 300 µm. The film may be single layered or multi-layered.

Examples of synthetic polymers include polyethylene terephthalate (PET), polystyrene, polyethylene, polypropylene, polyvinylchloride, polyamide, polyvinylidenchloride, polyethylenvinyl alcohol, polyethylene vinyl acetate, neoprene, polyurethane, latex, nylon, nitrile rubber and silicone, for example, silicone wafer. The synthetic polymer may be a biodegradable polymer. Examples of biodegradable polymers are polylactic acid (PLA) and polyglycolic acid (PGA). When used for packaging, the synthetic polymer is preferably PET as this polymer is widely used in food packaging.

Polystyrene is an aromatic polymer made from monomer styrene and has a range of applications. The bioflavonoid coating may be present on the surface of a rigid polystyrene material or in the case of a foamed or open-cell polystyrene material, the bioflavonoid coating may diffuse into the material so that it is present on surfaces within the foamed or open-cell structure.

The thickness of the bioflavonoid coating on the polymeric material is at least 50 nm, preferably at least 100 nm, more preferably between 700 and 1300 nm. These optimal coating thicknesses yield surfaces exhibiting antimicrobial and antioxidant performance for a longer period of time after bioflavonoid coating deposition.

Preferably, the bioflavonoid coating has a high surface roughness. Surface roughness is the measure of texture of a surface and is most often measured by the parameter $R_a$, which is the mean value for a randomly sampled area. It is quantified by the vertical deviations of a real surface from its ideal form. The average surface roughness ($R_a$) of the bioflavonoid coating is at least 100 nm, preferably between 600 and 1500 nm, more preferably between 800 and 1400 nm. Increased surface roughness yields surfaces exhibiting antimicrobial and antioxidant performance for a longer period of time after application of the bioflavonoid coating.

The term coating is understood to mean a covering of particles present on the surface of a polymeric material or in the case of a polymer with a foamed or open-cell structure, such as polystyrene, coating can occur on surfaces within the structure. It will be understood by the skilled person that the coating will not necessarily occupy the whole area of the surface which is intended to be covered, but may only cover, for example, 80% of the total area.

Even though it is appreciated that, for example, only 80% of the total area is covered in the coating, it is intended that the coating composition is evenly distributed across the whole of the surface area which is intended to be covered to form a homogenous coating. Use of a spray technique to apply the bioflavonoid coating to polymeric materials provides coatings with the highest surface homogeneity.

In one embodiment, the surface coverage of the bioflavonoid coating on the polymeric material is at least 50%, preferably at least 60%, more preferably between 70% and 100% of the total area to be covered.

In some embodiments only part of the area of the polymeric material will be coated, for example, only one component of a medical device.

In other embodiments only one part of the area of the polymeric material will be coated, for example, only one side of a polymeric film. The polymeric film may be used to package fresh produce, such as meat, and so in some instances only the side of the film which is in contact with the fresh produce will be coated. A further example of partial polymeric coating is when only the inside of a packaging tray is coated, for example, a food packaging tray used for storing and displaying meat or when only the inside of fruit packaging is coated.

A variety of different factors can cause fresh produce, such as meat, fish, fruit and vegetables to spoil which include microorganisms, exposure to air and poor packaging and storage. Food-borne microorganisms can be classified as either food-spoilage or food-poisoning microorganisms.

Food-spoilage microorganisms include moulds and bacteria. In meat, these microorganisms are responsible for detrimental quality changes which can include discoloration and unpleasant odours. Common spoilage bacteria include *Pseudomonas, Acinetobacter* and *Moraxella*.

Food-poisoning microorganisms can cause health problems by either intoxication or infection. Intoxicating microorganisms include *Clostridium perfringens, Staphylococcus aureus* (*S. aureus*) and *Clostridium botulinum*. These microorganisms produce a toxin when ingested by the host which then generally leads to sickness. Infection microorganisms include *Salmonella, Escherichia coli* (*E. coli*), *Campylobacter jejuni* and *Listeria monocytogenes*. These microorganisms grow inside a host once ingested and, like intoxicating microorganisms, cause severe sickness.

The coating compositions of the present invention show activity against a wide range of organisms including gram positive bacteria, gram negative bacteria, fungi, virus, protazoans and insect parasites. The coating compositions may be employed against difficult bacteria such as methicillin resistant *Staphylococcus aureus* (MRSA), *Clostridium difficile* (C. diff), *helicobacter pyroli* (H.py), and vancomycin resistant enterobacteria. The coating compositions of this invention may also be used against norovirus and other pathogens whereby transmission is by contact on air.

In particular, the coating composition described herein shows activity against *E. coli, S. aureus* and *Salmonella*. When poultry is packaged in the polymeric materials of the present invention it has been shown that the amount of these organisms present on the poultry is significantly reduced. The low levels of organisms present on the poultry results in a prolonged shelf life and improved quality of the poultry produce.

Another factor which affects the quality and shelf life of a meat product is oxidation. Antioxidants are often applied to meat product to prolong its shelf life. Either synthetic or natural antioxidants may be used, although natural antioxidants are preferred. As well as reducing the bacteria count on meat, the polymeric materials of the present invention also prevent the oxidation of meat due to the bioflavonoid coating.

According to a second aspect of the invention, there is provided use of a compound of Formula (I), as described herein, for coating the polymeric materials described herein.

Such polymeric materials may be used in packaging, for example food packaging and in particular, the packaging of fresh produce. In particular, the polymeric materials may be used in meat packaging, especially poultry packaging, for example turkey or chicken packaging, to reduce the bacterial count on the polymeric surfaces. The polymeric materials may also be used in the packaging of fish and shellfish, for example, salmon and prawns; and also fruit and vegetables, for example, soft fruits and salad leaves.

Examples of meat include beef, lamb, pork, bacon and poultry. Examples of poultry include chicken, quail, turkey, duck, goose, pigeon, dove, pheasant, ostrich, Indian reafowl, guinea fowl and rhea.

Poultry packaging falls into two categories, fresh and frozen. Different elements of poultry packaging include trays, films, wraps, boxes and napkins.

When presented in supermarkets, poultry will be presented in packaging in order to display the meat in an attractive way to consumers. The packaging also acts to prolong the shelf life of the product and ease shipping and handling of the product from the source where the meat is packaged to the shelf in the supermarket or grocers.

Meat, for example poultry, will usually sit in a tray which is often made of polystyrene or PET. A sealed environment will then be formed in order to prolong the shelf life of the poultry by restricting the amount of air in contact with the poultry product. One example is to use a film overwrap to cover the open edge of a tray in order to provide a contained environment for the poultry. Alternatively, a polymeric film is used to encase both the poultry and the tray to form an enclosed environment. Another example involves vacuum packing the poultry and tray with a polymeric film. In each of these examples, the inside of the film which forms the inside of the closed environment, is coated with the bioflavonoid coating described herein. In addition to the film being coated, the inside of the tray may also be coated with the bioflavonoid composition.

Other examples of packaging include polymeric bags such as flow pack wrappers (HFFS). This involves horizontal packing of the food produce using a single film coil with three weldings, two cross-weldings and one longitudinal welding to form a bag-like package. The single film may be coated with the bioflavonoid coating described herein.

When meat is packaged into a tray, the tray may further comprise a napkin, also known as a food pad, which sits on the base of the tray. The meat sits on the napkin which acts to absorb any juice from the meat. Meat juice can be quite unsightly and use of the napkin makes the meat product look more attractive on the shop shelves.

These napkins, or food pads, are also known as blankets and are also useful in the packaging of fruits, in particular, soft fruits. In the packaging of fruits, the napkin will sit on the base of the tray and the fruit will sit on top of the napkin. The napkin acts to cushion the fruit and absorb any juice. Soft fruits include figs, grapes and berries such as blackberries, raspberries, loganberries, blueberries, strawberries and the like.

The napkin is made of an absorbent material. In general, the napkin is made of a cellulosic or synthetic polymeric material, or a combination of both. For example, the napkin may be made up of several layers, including for example, a synthetic polymeric top layer and bottom layer with a cellulosic middle layer to provide maximum absorbency. A suitable synthetic polymeric material is, for example, polyethylene. The synthetic polymer may be a bioflavonoid coated synthetic polymer according to the invention.

Meat may also be packaged in resealable bags or pouches with a zip lock or similar fastening. In this instance the inside of the polymeric bag or pouch is coated with the bioflavonoid coating described herein. As well as the meat being packaged in such bags for transportation or for display in supermarkets, supplies of empty bags or pouches coated with the bioflavonoid coating described herein may also be sold to consumers to use at home to freeze, refrigerate or store meat. Bioflavonoid coated resealable bags and pouches may also be useful for the packaging of fish, shellfish, fruit, vegetables and other fresh food produce. For example, soft fruits including berries and grapes, salad leaves including spinach and lettuce, herbs, spring onions and the like may be packaged in the bags and pouches. In fact, any fish, shellfish, fruit or vegetables which are packaged in polymeric bags or pouches for transportation or display in supermarkets can be packaged in the bioflavonoid coated materials of the present invention. Sealed bags and pouches which are not resealable are also contemplated.

As well as packaging the meat in the bioflavonoid coated packaging material, the meat may first be misted or sprayed with the bioflavonoid coating to reduce the bacteria count on the meat and prevent oxidation. The meat may be misted or sprayed before being packaged; alternatively, the meat is misted or sprayed whilst in the packaging tray but before a film is applied to seal the package.

The meat so treated may be a meat hereinbefore described but it is very aptly packaged chicken or turkey, particularly chicken.

Preferably the bioflavonoid coating is applied to the side of the film or packaging enclosing the fresh produce, i.e. the inside of the packaging. Alternatively or additionally, the bioflavonoid coating may also be applied to the outside of the film or packaging, i.e. the side of the packaging which is exposed to the air and human contact. Application of the bioflavonoid coating to the outside of the packaging reduces the bacterial count on the side of the packaging which comes into contact with handlers at each stage of the production and shipment process and finally by the end the user. This prevents handlers of the packaging from coming into contact with harmful microorganisms which may be present on the outer surface of the packaging.

In another embodiment, the coated polymeric materials of the present invention may be used to provide sterile medical devices, for example, catheters, cannulas, oral prostheses and joint replacement components such as hip, knee and spinal implants.

Catheters are made from polymers such as silicone rubber, nylon, polyurethane, polyethylene terephthalate (PET), latex and thermoplastic elastomers. The choice of polymer can depend upon the application of the catheter and therefore the degree of flexibility required. Joint replacement components are often made of ultra-high-molecular-weight polyethylene (UHMWPE). Creating a clean, sterile environment when handling catheters, cannulas, joint replacement components and the like is key to preventing infection and having a bioflavonoid coated device helps greatly in achieving such a sterile environment.

In a further embodiment, bioflavonoid coated synthetic polymers may be used in the field of protective face masks, for example respiratory masks, as it provides enhanced protection for the user against inhaling bacteria and viruses. Polystyrene is particularly preferred. The masks may be reusable or disposable. Methods of manufacturing face masks are well known in the art.

Bioflavonoid coated polystyrene in the form of beads, beans or balls may be used in packaging to provide improved protection for sterile goods.

There is also provided a process for applying a coating comprising a compound of Formula (I), as described herein, to a polymeric material.

The polymeric material may be coated by immersion with the bioflavonoid coating. Using an immersion technique involves immersing the polymeric material in a solution of the bioflavonoid coating at a constant speed. The polymeric material is then pulled up out of the solution allowing a thin film of coating to deposit itself on the surface of the material whilst it is pulled up out of the solution. The speed at which the material is pulled up out of the solution remains constant so as to produce an even deposition of the coating solution. Control of the speed also allows the thickness of the coating to be controlled. The polymeric material is then dried and the solvent in the coating solution evaporates leaving behind a film of bioflavonoid coating on the polymeric material. Variations of this technique will be known to the skilled person.

Alternatively, the polymeric material may be coated by spraying with a dry or wet mist of the bioflavonoid coating. One method of spraying involves using the nebulizers incorporated into plasma treatment systems. Other methods of spraying will be known to the skilled person.

For the immersion and spraying techniques the bioflavonoid coating composition is preferably dissolved in an organic solvent prior to application to the polymeric material to create a solution. A suitable organic solvent includes methanol. Other suitable organic solvents will be known to the skilled person. The solution may comprise between 10 and 15% (wt/wt) of the coating composition in the organic solvent, preferably 15% (wt/wt) of the coating composition is used.

Alternatively, the polymeric material may be coated by surface blasting with the coating composition. Surface blasting methods include laser ablation and sputter deposition. Other suitable methods will be known to the skilled person.

Preferably, the polymeric material undergoes plasma pre-treatment prior to application of the bioflavonoid coating. The plasma treatment may be atmospheric pressure treatment or plasma immersion ion implantation (PIII) treatment. The atmospheric pressure treatment could be either helium based, argon based, air based, or a mixture of either helium or argon with air. Examples of suitable atmospheric plasma systems are LabLine™, PlasmaStream™ and PlasmaTreat. The substantial increase in thickness and roughness achieved for the coatings deposited onto the pre-treated polymers result in enhanced antibacterial effectiveness.

Polymers generally have low surface energy leading to problems such as poor wettability, dyeability and adhesion. A large range of techniques have been developed to overcome this problem. These include the use of chemical treatments, flame, corona as well as both low pressure and atmospheric pressure plasmas. Plasma treatment is a surface treatment which exposes polymers to partially ionized gas. The ionized gas is used at either low pressure or atmospheric pressure to increase the polymer surface energy.

A particular advantage of plasma treatments for activating polymers is the uniformity of the treatment. The depth of modification with plasma treatments is generally less than 10 nm. One of its effects is to enhance crosslinking and as a result weak boundary layers can be removed, hence strengthening the adhesive bond. Chain scissioning of the long polymer molecules may also occur, thus generating chemical sites which are available for bonding with an adhesive. For example, the incorporation of functional groups containing oxygen and nitrogen into the surface has been demonstrated after plasma activation. It has been shown that even if only a few chemical sites are created there will be a large increase in adhesive strength. Removal of surface contaminants is also an important contribution of plasma treatment to polymer adhesion.

It has been found that plasma activation of polymer and other substrates such as silicon wafers prior to the spray deposition of the antibacterial coating increases both the thickness and roughness of the bioflavonoid layer deposited by spraying. The use of plasma pre-treatment substantially increases both the thickness and roughness of the bioflavonoid layer deposited. The increased thickness of the deposited bioflavonoid layer seems to be associated with the increased surface energy which increases the attachment of the nebulized droplets to the surface, without compromising the antibacterial or antioxidant activity of the bioflavonoid coating (e.g. covalent immobilization may block the chemical groups that are essential for antibacterial or antioxidant function). As illustrated in FIG. 1, an increase in bioflavonoid coating thickness was obtained as the substrate water contact angle was systematically reduced (indicative of higher substrate surface energy). This increased thickness increases the longevity of the antioxidant and antibacterial properties of the coating. For a given coating thickness an increased surface roughness results in the coated polymeric material displaying enhanced levels of antioxidant activity as well as greater antibacterial activity.

Aptly the plasma treated polymeric material or polymer film to be coated will have a water contact angle (WCA) of less than 95°, more aptly less than 75°, favourably less than 60°, for example 35°-40°.A suitable method of measuring WCAs on the various substrates is the sessile drop technique, using an optical contact angle measuring instrument OCA 20 (Dataphysics Instruments GmbH, Filderstadt, Germany) at room temperature.

In an additional aspect of the invention, there is provided a packaged product wherein the product is formed of a synthetic polymeric material having a bioflavonoid coating of the present disclosure. The polymeric material and the bioflavonoid coating are as described in the first aspect of the invention.

The product may be in the form of a packaging tray, face mask such as a respiratory mask or a medical such as a catheter or cannula.

The product may be individually packaged. Alternatively, the product may be packaged as part of a multi-pack. Known packaging methods and materials may be used to package the products of the present invention, for example conventional filmic agents or cardboard boxes.

A bioflavonoid mixture particularly suitable for use in this invention is available as Citrox HX powder. This contains a mixture of bioflavonoids comprising at least 50% (wt/wt) of naringin and neohesperidin together with fruit acids; see for example Table 1.

In order that the invention may be more fully understood it will now be described, by way of example only, and with reference to the following Figure(s), in which:

BRIEF DESCRIPTION OF DRAWINGS

FIG. 1—Comparison between the Citrox coating thicknesses with water contact angle (WCA) obtained after PET treatment with either the PlasmaTreat PT (air) and PlasmaStream™ PS (helium/oxygen) plasmas.

FIG. 2—Comparison between the Citrox coating roughness with water contact angle (WCA) obtained after PET treatment with either the PlasmaTreat PT (air) and PlasmaStream™ PS (helium/oxygen) plasmas.

FIG. 3—Effect of Citrox and vitamin E coatings, onto non $He/O_2$ pre-treated PET trays, after 2 passes of flow rate 100 μl/min, onto turkey oxidation, using the PlasmaStream™ system.

FIG. 4—Characteristic profilometry image of Citrox coating onto a non $He/O_2$ pre-treated silicon substrate, after 100 passes using the Labline™ system, one day after treatment (Magnification 2.6×).

FIG. 5—Characteristic profilometry image of Citrox coating onto a $He/O_2$ pre-treated silicon substrate, after 100 passes using the Labline™ system, one day after treatment (Magnification 2.6×).

FIG. 6—Effect of ageing time on the average surface roughness ($R_a$) of Citrox (15%) coatings onto the $He/O_2$ and non pre-treated silicon substrates, after 100 passes using the Labline™ system.

FIG. 7—Effect of ageing time on the thickness of Citrox (15%) coatings onto the $He/O_2$ and non pre-treated silicon substrates, after 100 passes using the Labline™ system.

FIG. 8—Characteristic profilometry image of Citrox coating onto a non $He/O_2$ pre-treated silicon substrate after 100 passes using the Labline™ system, twenty one days after treatment (Magnification 2.6×).

FIG. 9—Characteristic profilometry image of Citrox coating onto a $He/O_2$ pre-treated silicon substrate after 100 passes using the Labline™ system, twenty one days after treatment (Magnification 2.6×).

FIG. 10—Antibacterial activity, against *S. aureus*, of Citrox coating onto the $He/O_2$ and non pre-treated PET substrates after 100 passes using the Labline™ system, as a function of time.

FIG. 11—Antibacterial activity, against *E. coli*, of Citrox coating onto the $He/O_2$ and non pretreated PET substrates after 100 passes using the Labline™ system, as a function of time.

FIG. 12—Antibacterial activity, against *Salmonella*, of Citrox coating onto the $He/O_2$ and non pre-treated PET substrates after 100 passes using the Labline™ system, as a function of time.

FIG. 13—Antibacterial activity of Citrox against bacteria found on the chicken, the Citrox being sprayed either i) on a PET tray and then placing the chicken on top or ii) directly on the chicken, in comparison to the control that is chicken placed on a PET tray without any treatment. The antibacterial effect was measured on day 6 after spraying.

FIG. 14—FTIR ATR spectra in the range of 900 to 1900 $cm^{-1}$ showing the presence of Citrox on plasma treated and untreated polystyrene sheets after incubation with Citrox and subsequent washing with water. The blue line (or black line) represents untreated polystyrene. The red line (or grey line) represents plasma immersion ion implantation (PIII).

FIG. 15—FTIR ATR spectra in the range of 2400 to 3900 $cm^{-1}$ showing the presence of Citrox on plasma treated and untreated polystyrene sheets after incubation with Citrox and subsequent washing with water. The blue line (or black line) represents untreated polystyrene. The red line (or grey line) represents plasma immersion ion implantation (PIII).

The mixture of bioflavonoids employs bioflavonoids in admixture with biomass residues of extraction from bitter oranges. The bioflavonoid components comprise 40-50%, for example about 45% wt/wt of this mixture (HPLC-45). HPLC-45 is available from Exquim (the food arm of Grupo Ferrer) as Citrus Bioflavonoid Complex 45% HPLC.

Citrox HXT powder comprises on a wt/wt basis 7.5% HPLC 45, citric acid 30%, willow bark extract 50% and *Olea europaea* extract 12.5%. Citrox HXT powder is available from Citrox Biosciences, Limited, Huntington, UK.

The willow bark extract contains 90% of salicylic acid.

The *Olea europaea* extract contains 20% of oleuropein.

HPLC-45 contains 45% by weight of a mix of bioflavonoids together with residues of extraction from bitter oranges.

TABLE 1

The mixture of bioflavonoids in HPLC-45:

| Bioflavonoid | % bioflavonoid in mixture with biomass |
| --- | --- |
| Neoeriocitrin | 1.1 |
| Isonaringin | 1.2 |
| Naringin | 23.4 |
| Hesperidin | 1.4 |
| Neohesperidin | 12.5 |
| Neodiosmin | 1.4 |
| Naringenin | 1.5 |
| Poncirin | 2.0 |
| Other (Rhiofolin) | 0.5 |

EXAMPLES

Example 1

Experimental Methodology

Preparation of Citrox Precursor: Citrox HXT powder was dissolved in methanol. 10% or 15% (w/w) of Citrox in methanol was used to formulate the precursor.

Pre-treatment of Samples: the Polyethylene Terephthalate (PET) films and the silicon wafers were or were not initially He/$O_2$ plasma pre-treated.

In the case of the atmospheric Plasma Jet treatment systems (such as PlasmaStream™), the substrates were activated by two passes of a plasma formed with 5% $O_2$ in He. The applied plasma power was 80%, the CNC speed was 7 mm/sec and the substrate to plasma jet orifice distance was 10 mm.

In the case of a reel-to-reel atmospheric plasma (such as the Labline™ system), the substrates were activated by passing them three times through the treatment chamber containing a 5% $O_2$ in a He plasma formed between two dielectric plates. The applied plasma power was 1000 W and the samples passed through the chamber at a speed of 1.5 m/min.

Citrox coatings were deposited onto the plasma pre-treated or non pre-treated PET films and silicon wafers, using the nebulizers incorporated in the PlasmaStream™, Labline™ and PlasmaTreat systems. The use of a Citrox immersion technique was also evaluated as an alternative to spraying however the immersion method did not lead to a homogeneous coating. The spray technique yields coatings with the highest surface roughness and homogeneity.

In the case of the PlasmaStream™ system, the depositions were carried out using the 10% of Citrox in a methanol precursor under three flow rates: 25, 50 and 100 µl/min and the number of passes varied between 2 and 16. Deposition parameters such as He flow rate, CNC speed and substrate to plasma jet orifice distance were kept constant at 5 l/min, 7 mm/sec and 2 mm respectively.

In the case of the Labline™ system, the depositions were carried out using the 10% or 15% of Citrox in methanol and the aeroneb pro micropumb nebulizer. The flow rate was constant: 0.2 ml/min. The number of passes varied between 5 and 150. Deposition parameters such as $N_2$ flow rate and speed were kept constant at 5 l/min and 1.5 m/min respectively.

Finally in the case of the PlasmaTreat system, the plasma treatment parameters were chosen so as to replicate the degree of activation achieved previously using the PlasmaStream™ system. Following an iterative study, the following PlasmaTreat parameters were chosen to activate the PET samples: 90% Voltage, 50% PCT, 20 kHz, 3000 mbar, 250 mm/sec cnc speed, and the substrate to jet nozzle distance was set to 15.5 mm.

Materials Characterization: The coatings were examined using optical microscopy, scanning electron microscopy (SEM), optical profilometry, water contact angle measurements, and Fourier transform infrared spectroscopy (FTIR).

Antibacterial Activity of the Citrox deposited onto PET films, either plasma activated or not plasma activated, was examined against three bacterial species: *S. aureus, E. coli* and *Salmonella*.

Antioxidant Activity of the Citrox deposited onto PET, either plasma activated or not plasma activated, was examined against turkey oxidation.

Results

1. Plasma Jet Systems—Influence of Flow Rate/Number of Passes on Citrox Layer Thickness and Morphology From earlier studies it has been concluded that the activity of Citrox is dependent on the thickness of the deposited layer and possibly the surface roughness. The objective of this study was to determine how Citrox flow rate through the nebulizer influences the roughness and thickness of the Citrox coatings deposited onto silicon wafer substrates. In this study no pre-plasma activation was carried out. It is concluded that at flow rates of 25, 50 and 100 µl/min, where the overall quantity of Citrox deposited is constant, that the $R_a$ values are broadly similar. The thickness results also indicate that when the same total concentration is deposited it does not matter with respect to thickness if the layer is deposited for example from 8×25 μl/min or 2×100 μl/min.

When pre-activation of the substrate is carried out using a plasma, substantially increased levels of Citrox coating adhesion is obtained when all other deposition parameters are fixed. As demonstrated in FIG. 1, nearly a threefold increase in the level of adherent Citrox is obtained after plasma activation (substrate contact angle 15°). This figure also illustrates the minimal effect of changing the helium/oxygen plasma (PlasmaStream™ (PS) system) for an air plasma (PlasmaTreat (PT) system) for the activation of PET. The level of Citrox attachment was found to be dependent on the water contact angle (WCA). At lower water contact angles (higher surface energy), higher levels of Citrox was found to adhere. The surface roughness results (FIG. 2) were found as expected to increase with an increase in the Citrox coating thickness. Note the very similar Citrox coating thickness and roughness values obtained for a given contact angle achieved with both the air and helium jet plasmas. The advantage of using the former is the significantly reduced processing costs in using an air plasma.

Water Contact Angle Measurements and Fourier Transform Infrared Spectroscopy:

The water contact angle and FTIR spectra were obtained for the Citrox layers deposited at the different flow rates. In all cases the water contact angle of the citrox coatings were highly hydrophilic with a contact angle lower than 5°. FTIR confirmed the presence of bioflavonoids in the samples. The characteristic bands (aromatic between 1480 and 1637 $cm^{-1}$, —OH—phenolic at 1205, 1293, 1439 and 3476 $cm^{-1}$, methoxylic at 1248 $cm^{-1}$ and carbonylic at 1657 $cm^{-1}$) were in good agreement with the FTIR spectra of naringin and neohesperidin, showing that the chemical functionality is preserved during the deposition process.

Antibacterial Activity

The Citrox coatings showed bactericidal effects against *S. aureus*, when Citrox was deposited onto the non $He/O_2$ pre-treated substrates after either a) 4 passes of flow rate 50

µl/min or b) 2 passes of flow rate 100 µl/min. This test is obviously dependant on the concentration of bacteria exposed to the coated polymer and the ageing effect. In this study the concentration was 1×10$^8$ Colony Forming Units (CFUs)/ml and the samples were tested one day after deposition. It was concluded therefore that the minimum inhibitory thickness is 60 nm (the associated R$_a$ is 500 nm).

In the case of the PET polymer which had been treated to a He/O$_2$ plasma, a similar Citrox thickness and roughness is also required but in this case the bactericidal effect was achieved after 2 passes of flow rate 50 µl/min or b) 1 pass of flow rate 100 µl/min.

Antioxidant Activity

Figure 3:
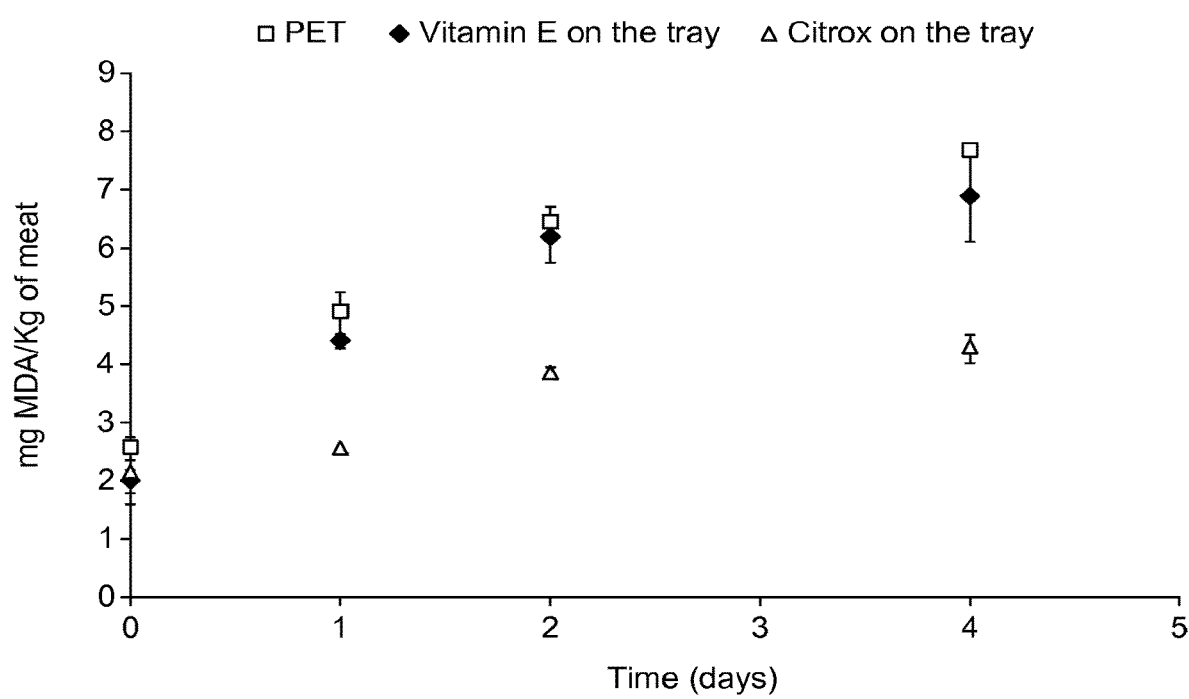
Figure 4:
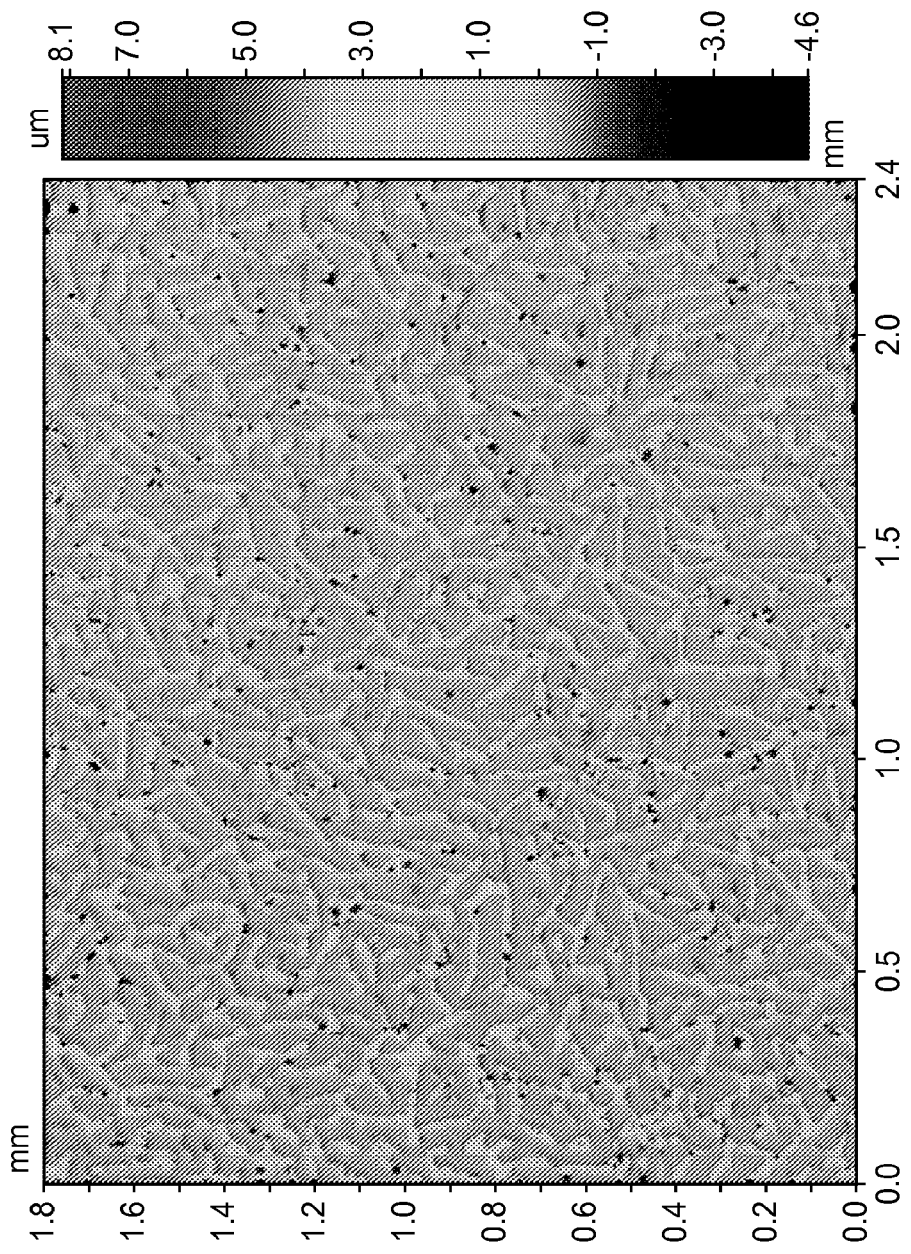
Figure 5:
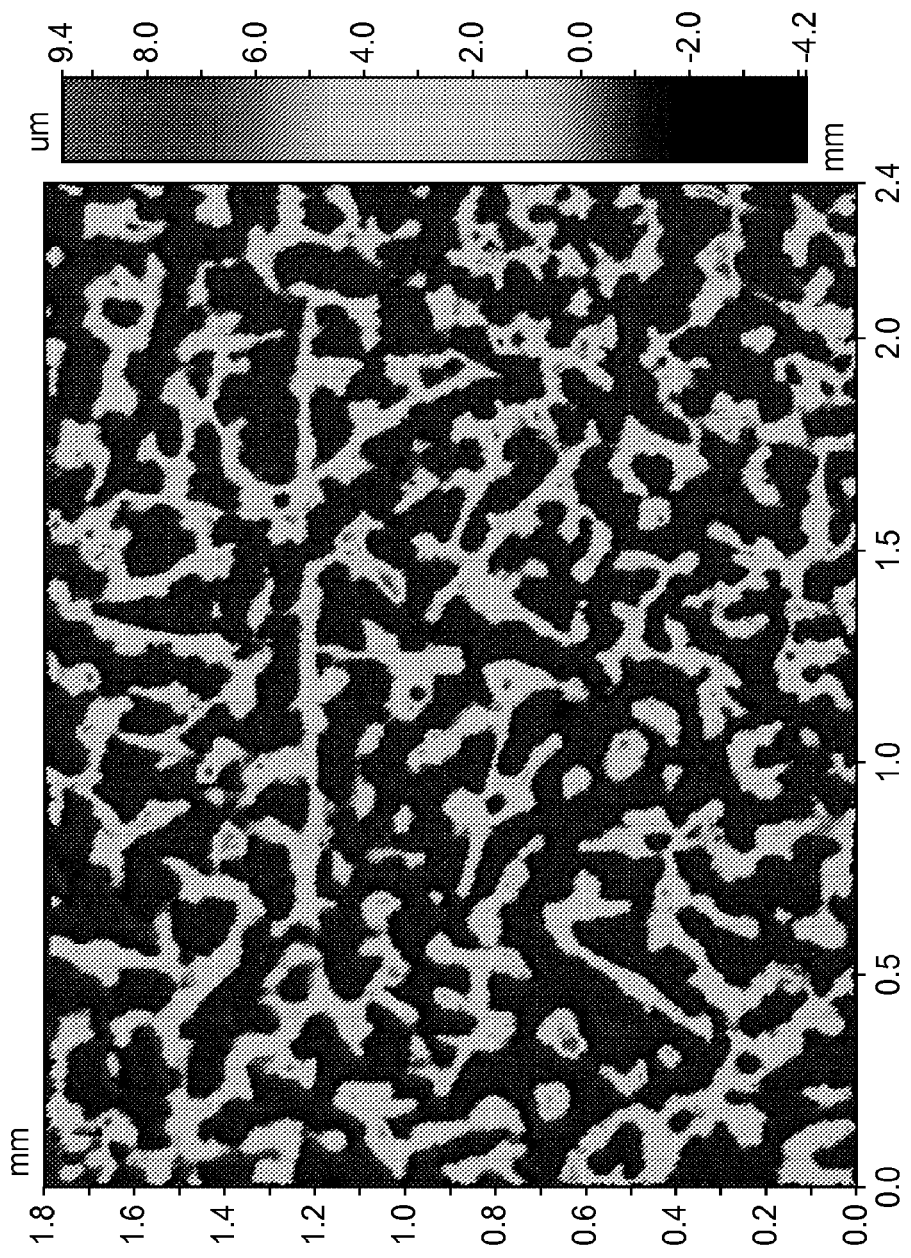

The examination of the antioxidant effect of Citrox and Vitamin E coatings deposited onto the non He/O$_2$ pre-treated PET substrates after 2 passes of flow rate 100 µl/min showed that Citrox is more effective than Vitamin E in reducing turkey oxidation with time (FIG. 3). Lipid oxidation is expressed as mg malonaldehyde (MDA)/kg of meat. Malonaldehyde is the product of polyunsaturated lipids degradation due to oxygen species. The higher the value the higher the oxidation.

2. Application of Citrox Coatings Using the Labline™ System—Influence of Number of Passes/Concentration on Citrox Layer Thickness and Morphology The objective of this study was to investigate the effect of using nebulizers mounted in either a reel-to-reel (Labline™) or atmospheric plasma jet (PlasmaStream™) system for the Citrox coating of plasma pre-activated PET polymers. In the case of this reel-to-reel web treatment system it was found that a much larger number of passes were required in order to obtain the same Citrox layer thickness and roughness as obtained using the PlasmaStream™ jet system. In this study the nebulizers used a precursor flow rate of 0.2 ml/min. A layer of thickness 60 nm in the case of the Plasma Jet system was achieved onto the non He/O$_2$ pre-treated substrates after 4 passes of flow rate 50 µl/min, whereas in the case of the Labline™ system, similar thickness (70 nm) was achieved after 50 passes of flow rate 0.2 ml/min. As far as roughness is concerned, samples produced by the PlasmaStream™ Jet system presented higher average surface roughness (R$_a$) (~500 nm) in comparison to the Labline™ system (R$_a$~100 nm), for samples that had similar thickness (~60-70 nm).

Citrox Coating Deposition Using the Labline™ System

The initial study focused on the influence of the number of passes on coating roughness and thickness. There was a broadly linear effect with these two parameters with the number of passes. The surface roughness was considerably lower than coatings with similar thickness deposited using the PlasmaStream™ system. For example in the case of the Labline™ system a thickness of ~70 nm gave an R$_a$ value of 100 nm while a similar thickness with the PlasmaStream™ system gave a corresponding surface roughness of 500 nm.

These Citrox coatings deposited at a concentration of 10% Citrox in methanol did not exhibit antibacterial activity. Studies were carried out at concentration of 20% but these mixtures could not be nebulized. The focus of the research therefore concentrated on 15% Citrox in methanol solutions. A large number of passes were also required in order for the coating to exhibit anti-bacterial activity against S. aureus. The effect of increasing the number of passes to 150 on both coating thickness and roughness was demonstrated. This study was carried out both with plasma activated and non plasma activated silicon wafers. Coating thicknesses and roughness values of several microns were obtained. An interesting observation is the effect of pre-treating the substrate with He/O$_2$ plasma prior to the application of the Citrox layer. It was observed that the coating morphology was very different with the plasma activated surfaces exhibiting much larger aggregates of Citrox particles. Surface coverage (as evaluated by using the Image J software) was considerably higher with the plasma activated silicon as detailed in Table 2. This Table compares Citrox (15%) coatings deposited using the Labline™ system after 100 passes. There was a dramatic increase in both coating roughness and thickness with the He/O$_2$ plasma treatment. This may be associated with the increase in water contact angle. In the case of the un-treated and plasma treated silicon wafers the contact angle values obtained were 68° to 20° respectively. The corresponding contact angles for the PET polymer were 71° to 55° respectively.

TABLE 2

Influence of He/O$_2$ plasma pre-treatment of silicon wafer substrates prior to the deposition of Citrox with 100 passes using the Labline ™ system.

| | Untreated wafer | Plasma treated wafer |
|---|---|---|
| Surface coverage (%) | 34% | 55% |
| Citrox layer thickness (nm) | 152 ± 17 | 1179 ± 89 |
| Citrox layer roughness R$_a$ (nm) | 619 ± 27 | 1350 ± 70 |

Antibacterial Activity

The Citrox coatings showed bactericidal effects against S. aureus, when citrox was deposited onto the He/O$_2$ or non pre-treated substrates after 100 and 150 passes. This means that the minimum inhibitory R$_a$ is 500 nm and the minimum inhibitory thickness is approximately 100 nm.

3. Ageing Effect Study of Labline™ Deposited Citrox Coatings

Figure 6:
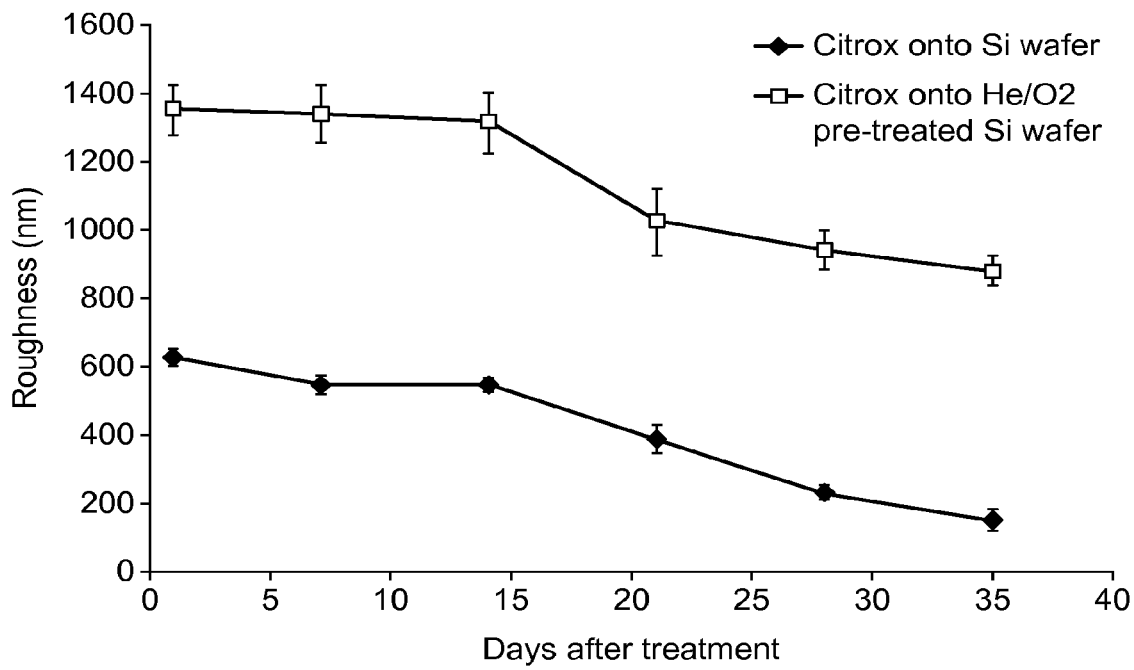
Figure 7:
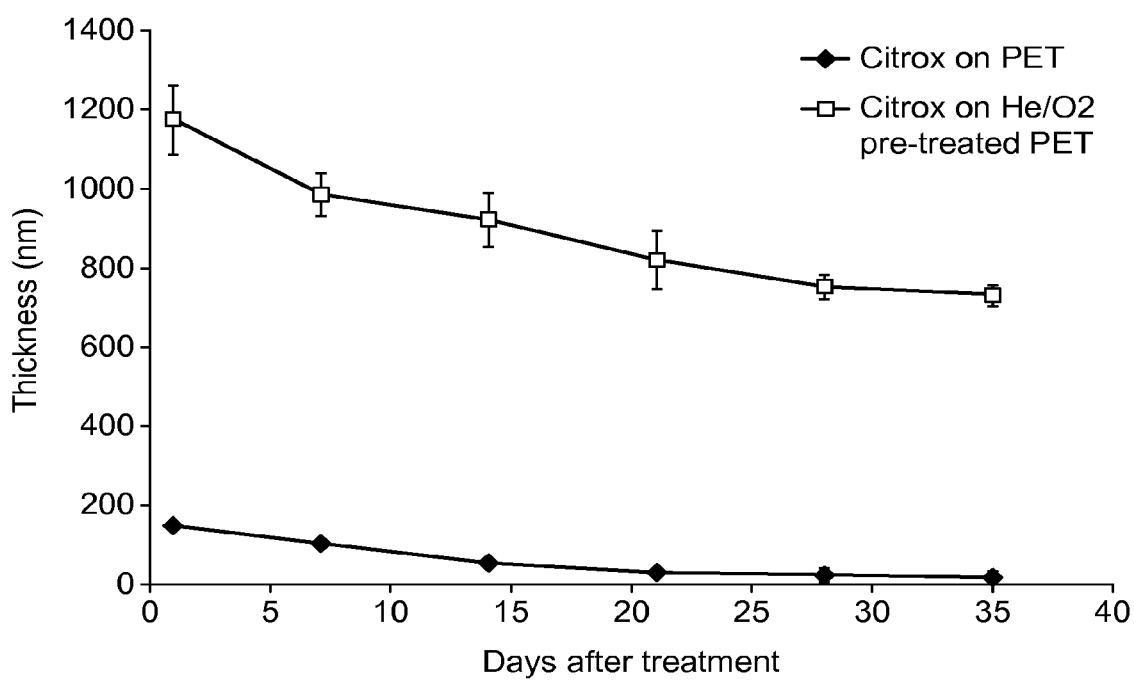
Figure 8:
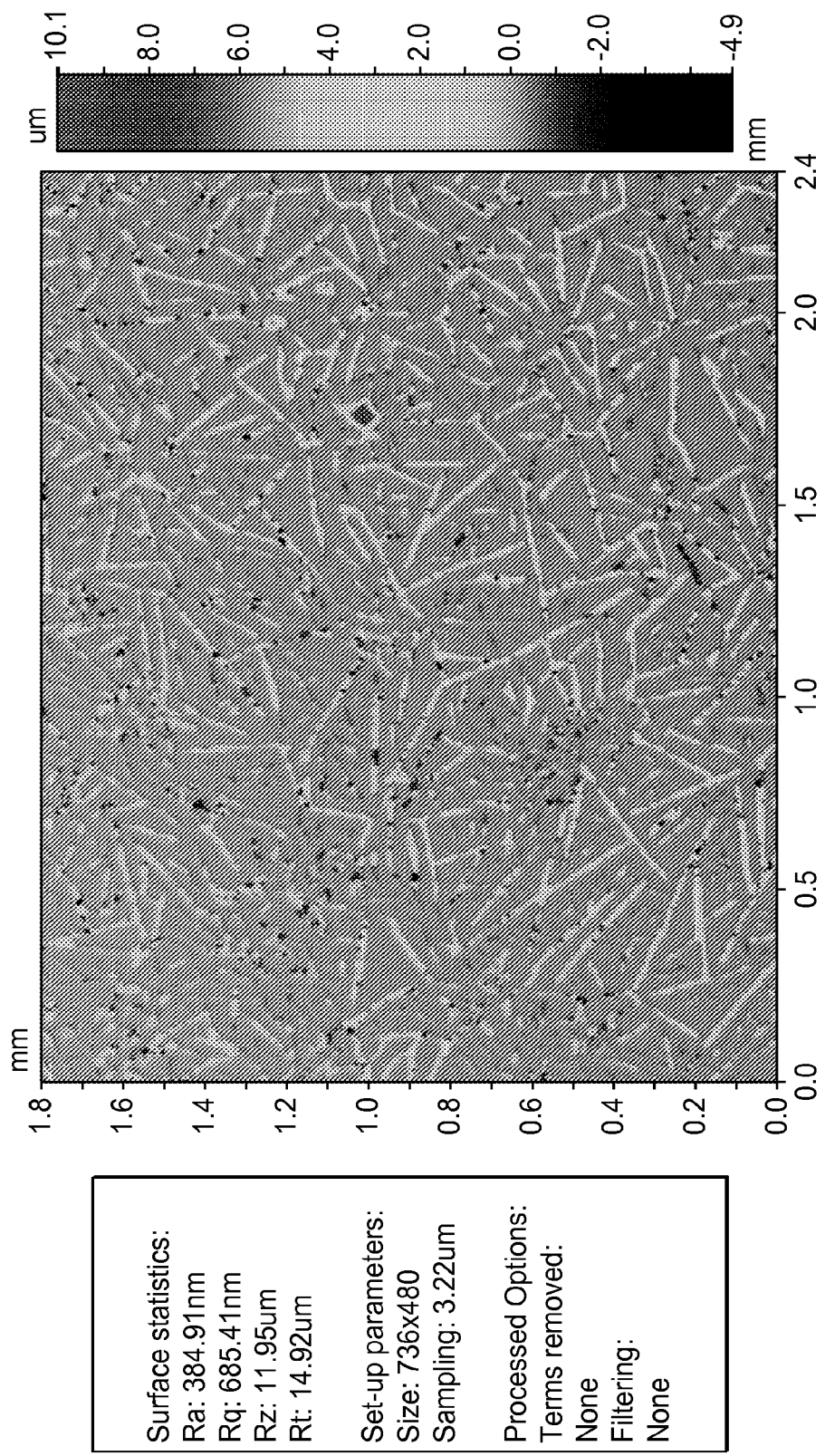
Figure 9:
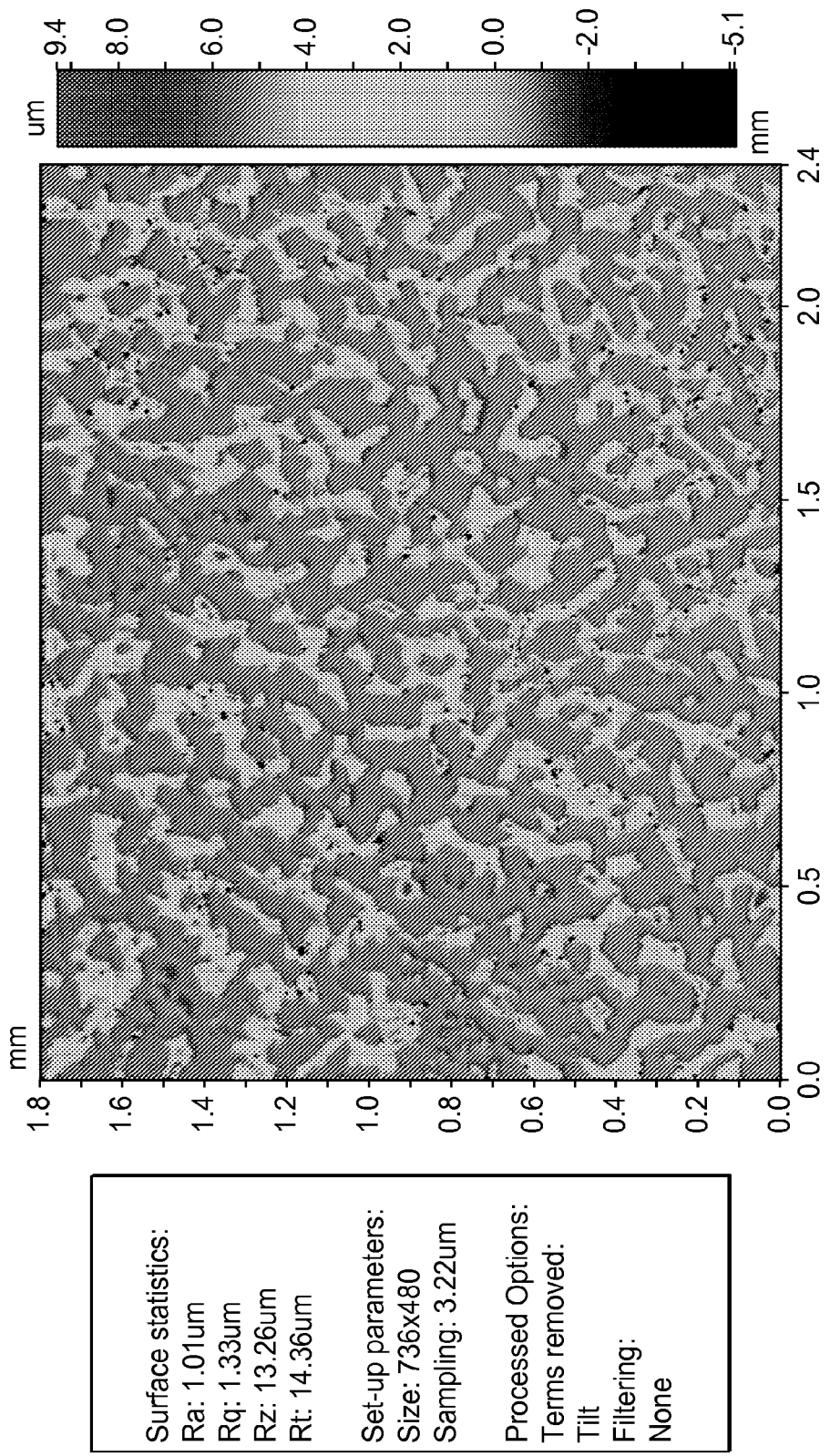

The objective of this study was to investigate if there was an ageing effect for Citrox deposited onto silicon wafer substrates. This investigation was carried out by measuring changes in both roughness and thickness with time after Citrox deposition. As illustrated in FIGS. 6 and 7 both these parameters decreased significantly during the 35 day study. Moreover, the surface coverage of the Si wafer by Citrox decreased from 55% to 47.6% in the case of the He/O$_2$ pre-treated substrate and from 34.4% to 23.3% in the case of the non He/O$_2$ pre-treated one, 35 days after treatment. This may be due to the loss of a volatile component in the Citrox/methanol layer.

FTIR was used to study changes in the relatively intensity of peaks with time. Overall peak intensity was observed to decrease with time. In particular, a decrease in the absolute intensity of the —OH phenolic band at 1200 cm-1 from 0.641 to 0.508 was observed 35 days after treatment in the case of the non He/O$_2$ pre-treated substrate, whereas in the case of the He/O$_2$ plasma pre-treatment the absolute intensity decreased from 0.862 to 0.726.

Antibacterial Activity

The objective of this study was to assess the longevity of the antibacterial effect of Citrox against S. aureus, E. coli and Salmonella. Citrox coatings were applied onto PET samples and the coated polymers were then stored by wrapping them in a polymer roll. The objective of this study was to determine if a roll of the coated polymer continued to exhibit antibacterial activity over time. The test samples were then removed from the roll just prior to the antibacterial study. It was attempted to correlate the level of antimicrobial activity with Citrox roughness and thickness.

Figure 10:
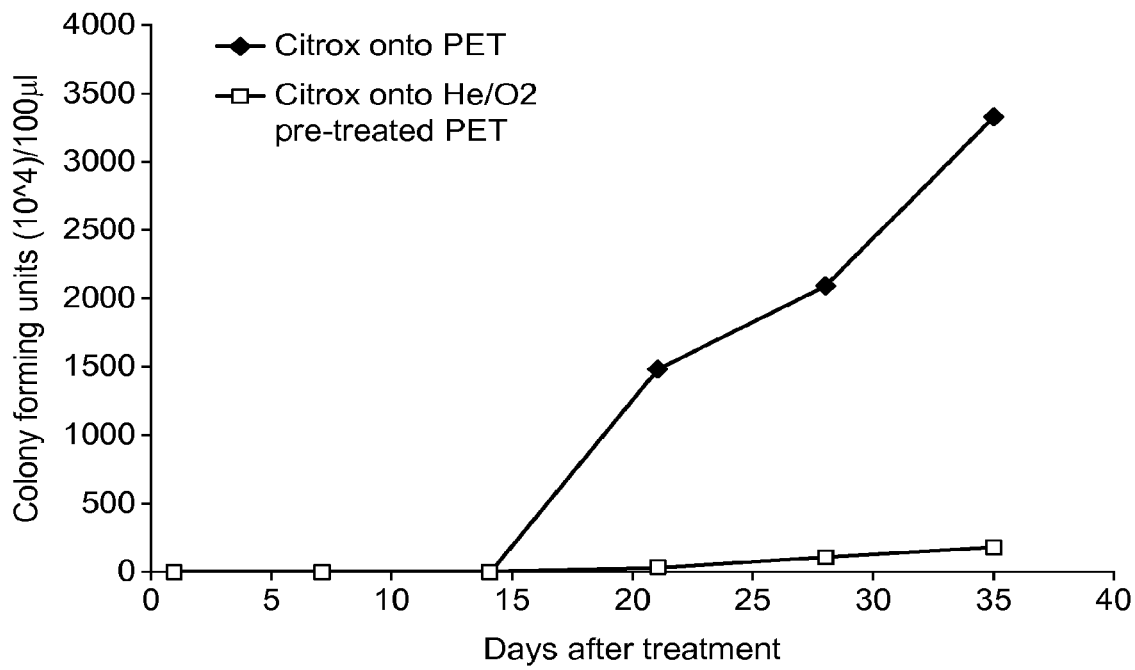
Figure 11:
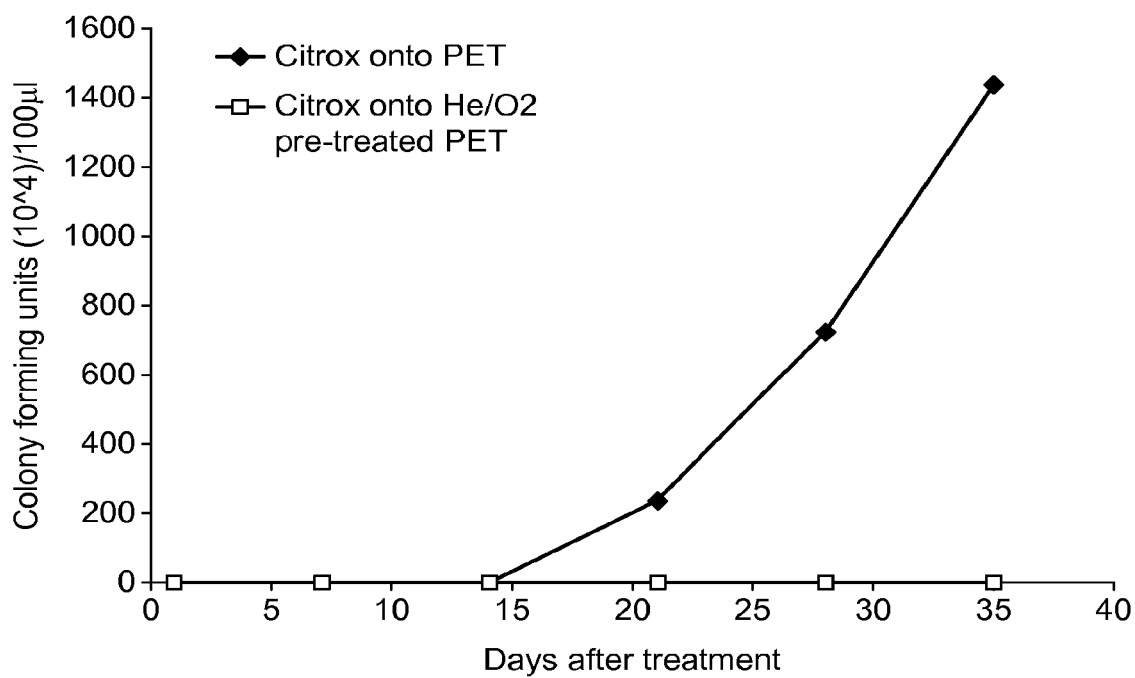
Figure 12:
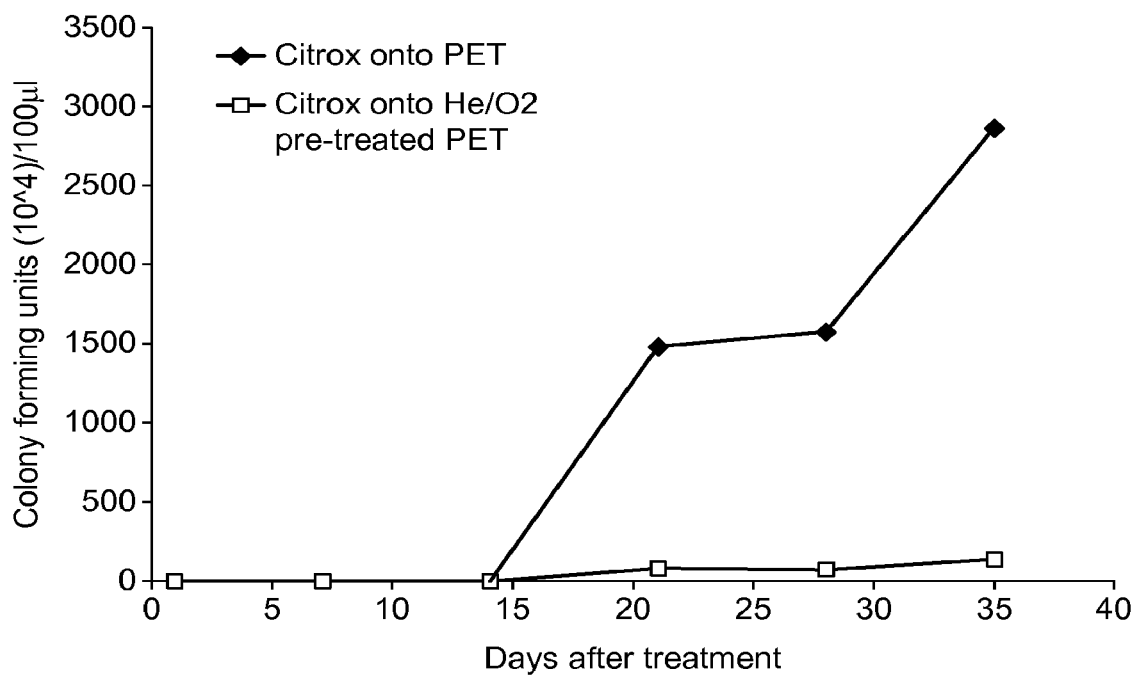

From FIGS. 10 to 12, which detail the level of anti-bacterial activity with time the following conclusions can be drawn—

The Citrox coatings showed bactericidal effects against *S. aureus* up to a period of 21 days, when Citrox was deposited onto the He/O$_2$ plasma pre-treated substrates, (100 passes, using the Labline™ system). A very small number of bacteria was observed on the test samples up to the completion of the 35 day test period indicating continued level of activity (FIG. 10). In the case of the Citrox coatings onto the non plasma treated substrates, with the same number of passes, the bactericidal effect was lost 21 days after Citrox deposition.

As illustrated in FIG. 11, the Citrox coatings showed a higher bactericidal effect against *E. coli* with no growth observed after 35 days of deposition, when Citrox was deposited onto the Labline™ He/O$_2$ plasma pre-treated substrates, after 100 passes. As before, for the Citrox coatings onto the non He/O$_2$ pre-treated substrates, the bactericidal effect was lost 21 days after Citrox deposition.

The Citrox coatings showed low *Salmonella* growth after 21 days of deposition, when Citrox was deposited onto the He/O$_2$ pre-treated substrates, after 100 passes using the Labline™ system. As before, for the non treated substrates, the bactericidal effect was lost 21 days after treatment. In the case of the plasma activated surface, in contrast, continued activity was observed up to the 35 day test period (FIG. 12).

FIGS. 10, 11 and 12 demonstrated the enhanced antibacterial performance of the Citrox coatings deposited on plasma activated polymers. The explanation for this is the substantial enhancement in thickness and roughness achieved for the coatings deposited on the pre-treated polymers. From these figures it is clear that very few bacteria adhere to the thicker and rougher coatings on the activated surfaces.

Figure 13:
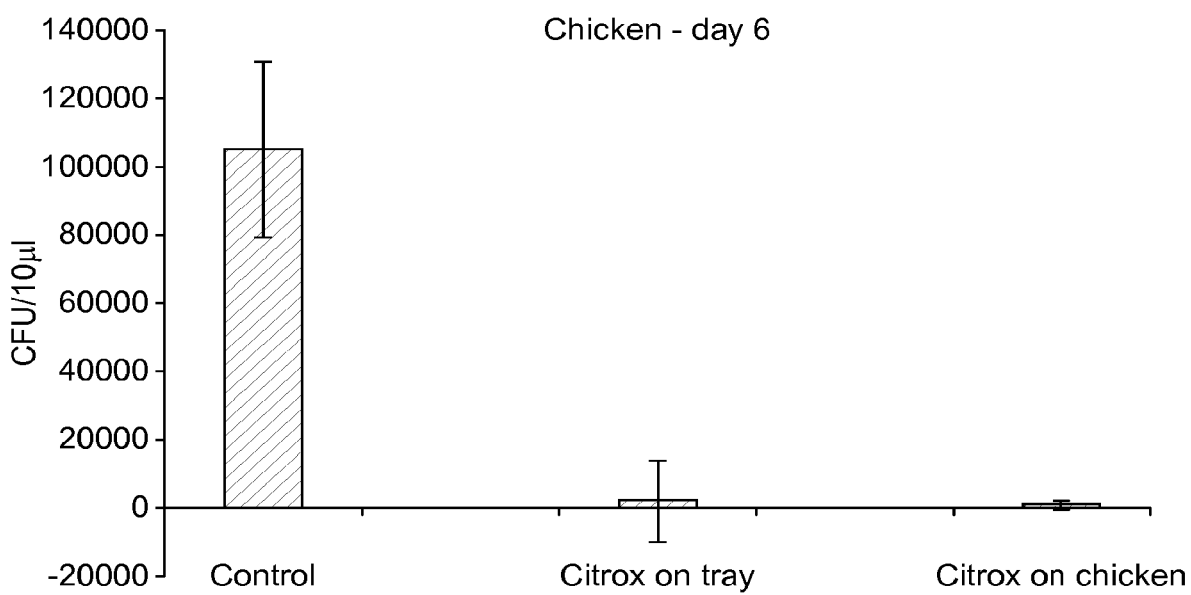
Figure 14:
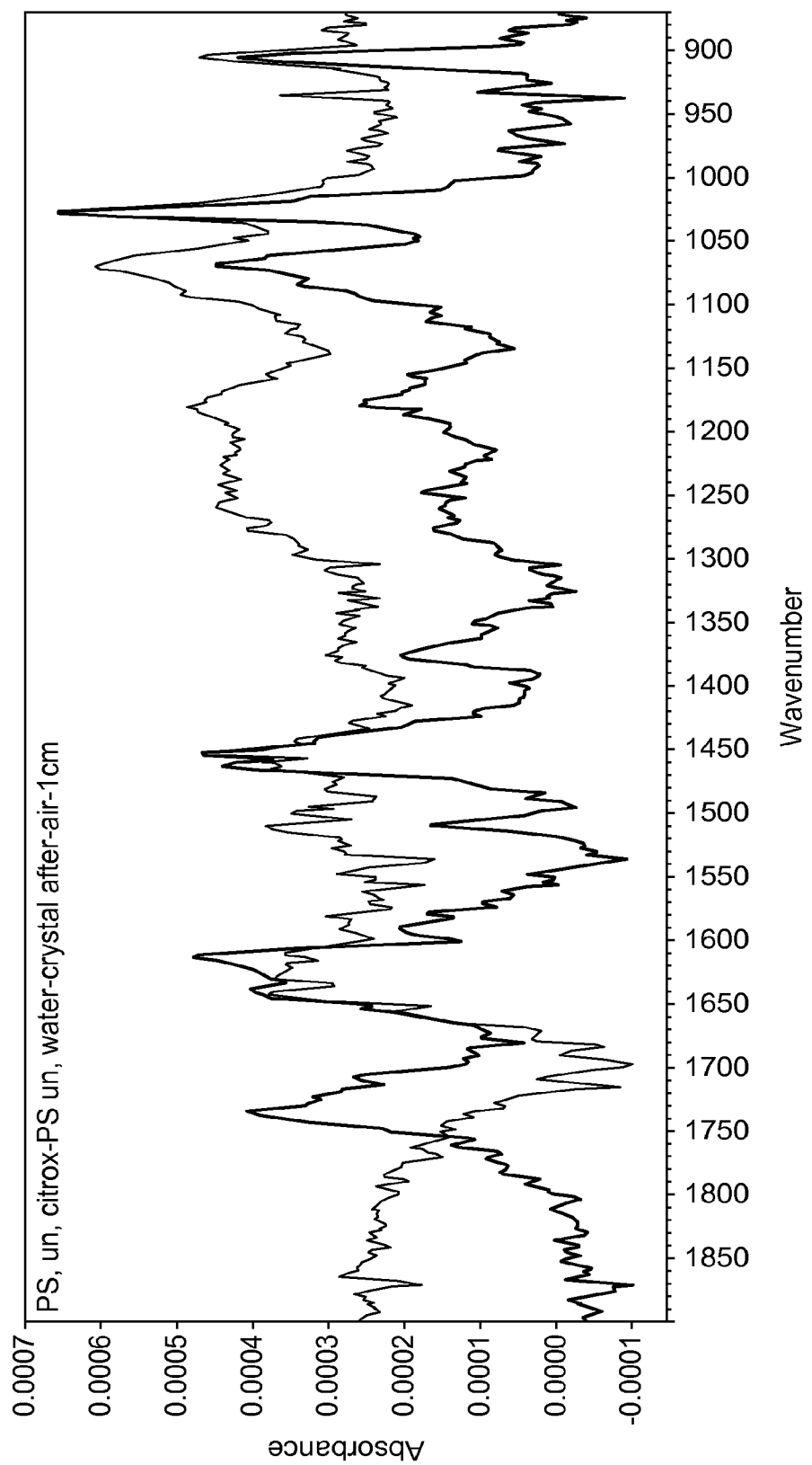
Figure 15:
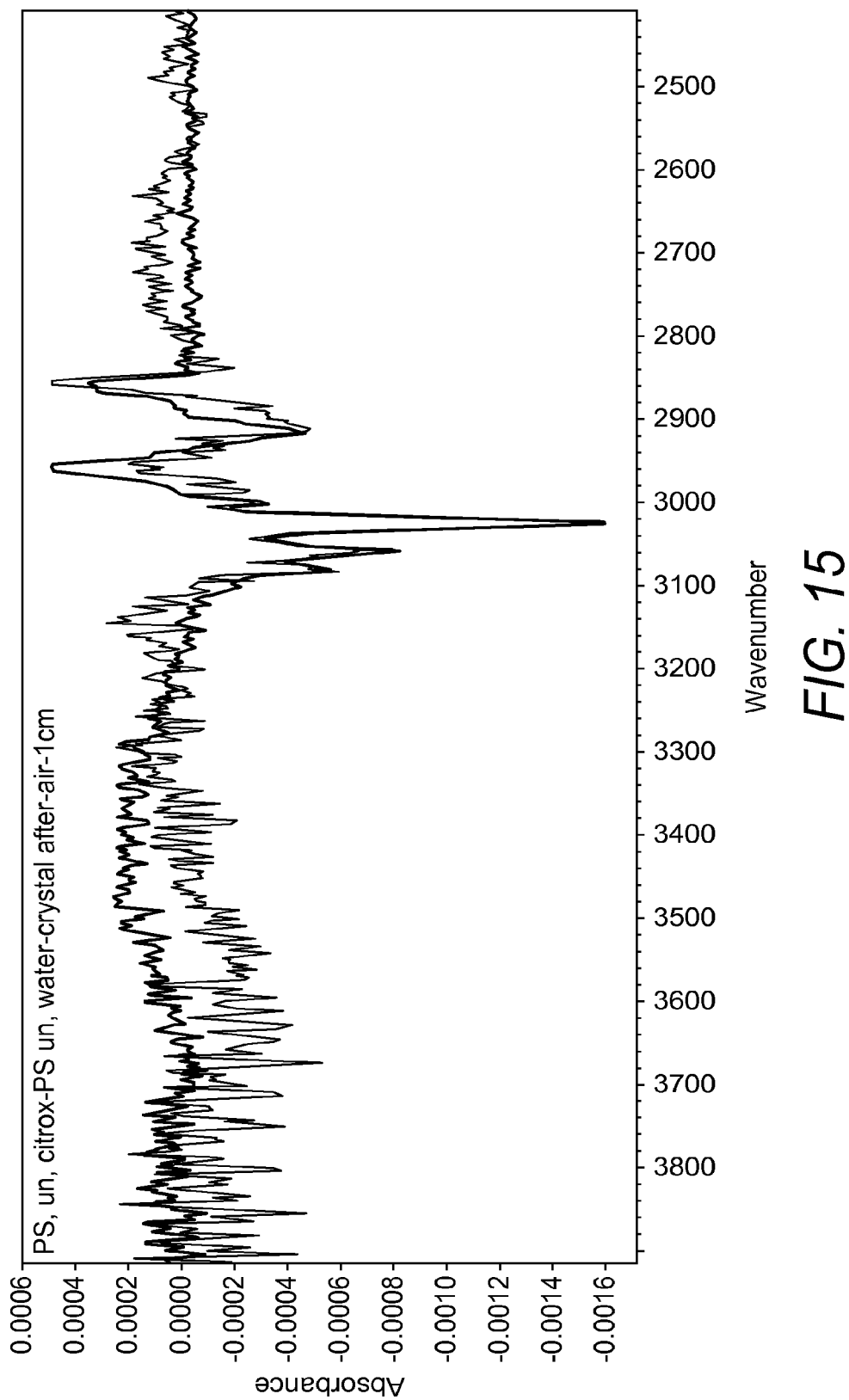

FIG. 13 demonstrates the effect of spraying Citrox, either i) on a PET tray and then placing the chicken on top or i) on the chicken, on bacterial viability, in comparison to control that is chicken that was placed on a PET tray without any treatment. The antibacterial effect was measured on day 6 after spraying.

Conclusions

The use of plasma pre-treatments substantially increases both the thickness and roughness of the Citrox layer deposited by spraying. For a given set of processing conditions up to a 3 fold increase in Citrox thickness was obtained on PET substrates and an 8 fold increase on silicon wafer substrates, which had been plasma pre-treated. This increase may be due to the higher energy surfaces enhancing the adhesion of the nebulized particles. The enhanced coating thickness yielded surfaces exhibiting antimicrobial performance longer periods after Citrox coating deposition.

Comparing the anti-microbial performance of Citrox coatings deposited using the Labline™ and PlasmaStream™ systems it is clear that in the case of the Labline™ system a Citrox layer thickness of ~70 nm is required, in contrast the thickness required using the PlasmaStream™ jet system was only ~50 nm. The corresponding surface roughness values are approximately 100 and 500 nm respectively. This result indicates that higher surface roughness is required to achieve higher levels of antibacterial activity with Citrox.
- Use of an immersion technique for the application of Citrox did not lead to a homogeneous coating. The spray technique yields coatings with the highest surface roughness and homogeneity.
- Citrox coatings deposited onto the He/$O_2$ plasma pre-treated substrates exhibited bactericidal effect against *S. aureus, E. coli* and *Salmonella* for a minimum of 35 days after the application of the Citrox layer (note very low levels of *S. aureus* and *Salmonella* observed after 21 days).
- A significant reduction in the level of turkey meat oxidation was observed after the application of Citrox onto PET trays. The antioxidant results compared favourably with Vitamin E coatings, a known commercial anti-oxidant.

Example 2

Impregnation of Polystyrene Sheets with Citrox

Polystyrene sheets were treated using plasma immersion ion implantation (PIII) with nitrogen ions of 20 keV energy for 800 seconds to create surface embedded radicals capable of covalently binding biologically active molecules (as described in Bilek et al, PNAS, 108(35):14405-14410, 2011, herein incorporated by reference). The PIII treated and untreated sheets were incubated in tubes containing Citrox concentrate (H PLC 45) or deionized water (for control) for 3 hours. In HPLC 45 or "Citrox BC" 45% (of the total composition of HPLC 45/Citrox BC) comprises bioflavonoids. The bioflavonoids are in admixture with biomass residues of extraction from bitter oranges, such as pectins, sugars and minor organic acids, which make up the remaining 55%. HPLC 45 is available from Exquim (a company of Grupo Ferrer) as Citrus Bioflavonoid Complex 45% HPLC. After incubation the sheets were washed intensively in tubes with deionized water (3 times with shaking for 20 minutes and changing the tubes each time). After washing the sheets were dried overnight.

FTIR ATR spectra were recorded with a Digilab spectrometer. The ATR crystal was Germanium trapezium, 45 degrees incident angle, 25 reflections. Spectral resolution was 4 $cm^{-1}$ and the number of scans was 500.

The spectra were analysed with Resolution-pro software. The spectra of the control samples were subtracted from that of the Citrox coated samples. The water vapour spectra and the Germanium crystal glue spectra were also subtracted. Baseline correction was done. The final spectra are presented in FIGS. 14 and 15.

The spectra show that the components of Citrox remain on untreated and PIII treated polystyrene sheets. The clear and intense lines at 910, 1040, 1070, 1460, 1510, 1620-1650, 2860-2980 $cm^{-1}$ are observed in the subtracted spectra for both untreated and treated sheets. The line in the range of 1750-1700 $cm^{-1}$ is present only in the spectra of the untreated sheets.

As the Germanium crystal was clean after contact with the sheets, the components of Citrox are strongly absorbed on the surface or diffused into bulk layers of the polystyrene sheets. Therefore, the Citrox components remain in the polystyrene sheets after incubation and washing with water.

Conclusions

- Plasma treated polystyrene sheets contain higher levels of Citrox.

The invention claimed is:

1. A respiratory mask comprising a synthetic polymeric material coated with a bioflavonoid coating, wherein a bioflavonoid content of the bioflavonoid coating comprises at least 50% wt/wt of a mixture of naringin and neohesperidin, and wherein the bioflavonoid coating comprises a thickness of between 700 nm and 1300 nm.

2. The respiratory mask of claim 1, wherein the mixture of naringin and neohesperidin comprises at least 70% wt/wt of the bioflavonoid content of the bioflavonoid coating.

3. The respiratory mask of claim 1, wherein the mixture of naringin and neohesperidin comprises between 75% to 80% wt/wt of the bioflavonoid content of the bioflavonoid coating.

4. The respiratory mask of claim 1, wherein the bioflavonoid content of the bioflavonoid coating further comprises one or more compounds selected from the group consisting of neoeriocitrin, isonaringin, hesperidin, neodiosmin, naringenin, poncirin and rhiofolin.

5. The respiratory mask of claim 1, wherein the bioflavonoid coating further comprises one or more fruit acids selected from the group consisting of salicylic acid, citric acid, lactic acid, ascorbic acid and malic acid.

6. An antimicrobial respiratory mask comprising a synthetic polymeric material coated with a bioflavonoid coating, wherein the average surface roughness of the bioflavonoid coating is between 600 nm and 1500 nm and wherein a bioflavonoid content of the bioflavonoid coating comprises at least 50% wt/wt of a mixture of naringin and neohesperidin and wherein said mask enhances protection of the user against inhaling bacteria and viruses.

7. The antimicrobial respiratory mask according to claim 6, wherein the synthetic polymer material comprises a film wherein said film comprises at least one synthetic polymer selected from the group comprising polyethylene terephthalate, polystyrene, polyethylene, polypropylene, polyvinylchloride, polyamide, polyvinylidene chloride, ethylene-vinyl alcohol co-polymer, polyethylene vinyl acetate, neoprene, polyurethane, nylon, latex, nitrile rubber and silicone.

* * * * *